United States Patent [19]

Elder et al.

[11] Patent Number: 4,794,168

[45] Date of Patent: * Dec. 27, 1988

[54] LEUKEMIA-ASSOCIATED VIRUS IMMUNOGEN, VACCINE AND ASSAY

[75] Inventors: John H. Elder, Cardiff; Richard A. Houghten, Solana Beach, both of Calif.

[73] Assignee: Scripps Clinic and Research Foundation, La Jolla, Calif.

[*] Notice: The portion of the term of this patent subsequent to May 5, 2004 has been disclaimed.

[21] Appl. No.: 813,279

[22] Filed: Dec. 10, 1985

Related U.S. Application Data

[63] Continuation-in-part of Ser. No. 603,348, Apr. 24, 1984, Pat. No. 4,663,436.

[51] Int. Cl.$^4$ .......................... C07K 7/06; C07K 7/08; C07K 7/10
[52] U.S. Cl. .................................. 530/324; 530/325; 530/326; 530/327
[58] Field of Search ................. 530/324, 325, 326, 327

[56] References Cited

FOREIGN PATENT DOCUMENTS

| | | |
|---|---|---|
| 0044710 | 1/1982 | European Pat. Off. . |
| 0119702 | 9/1984 | European Pat. Off. . |
| 0152030 | 8/1985 | European Pat. Off. . |
| WO85/02625 | 6/1985 | PCT Int'l Appl. . |

OTHER PUBLICATIONS

Elder et al., *J. Virol.*, 46:871–880 (1983).
Cianciolo et al., *Nature*, 311:515 (Oct. 1984).
Bayer et al., *EMBO J.*, 3:1925–1930 (1984).
Seiki et al., *Proc. Natl. Acad. Sci. U.S.A.*, 80:3618–3622 (1983).
Bosselman et al., *J. Virol.*, 44:19–31 (1982).
Chemical Abstracts, 104:207681j, (1986) (p. 801).

*Primary Examiner*—Delbert R. Phillips
*Attorney, Agent, or Firm*—Dressler, Goldsmith, Shore, Sutker & Milnamow, Ltd.

[57] ABSTRACT

The present invention relates to a leukemia-associated virus immunogens, vaccines, antibody combining sites and assays. The immunogens are relatively short polypeptides with peptide sequences corresponding to the antigenic determinant domains of a leukemia-associated virus envelope protein. The immunogens when introduced into a host stimulate the production of antibodies which immunoreact with the polypeptides and the leukemia-associated virus.

24 Claims, 8 Drawing Sheets

FIGURE 1

```
                   +-----I8B------C                    +----------------------I10B---------
                           10            20            30            40            50
FELV-B         ANF---SPHQVYNVTWTITNLVTGTKANATSMLGTLTDAFPTMYFDLCDIIGNTWNPSDQEP
FELV-B2                  I
F-MULV          A   GS           EV      GDRE-TVW  I  GNHP  WTWW     VLTP     MLALHGPPHWGL Y
AKV            VTLGN    F        EV      GDRE-TVW  ITGNHP  WTWW     DLTP     MLALHGPSYWGL Y
M-MULV          S   G    F       EV      GDRE-TVW  GNHP   WTWW     LTP      MLAHHGPSYWGL Y
M-MCF          QHD--              RV          QT V    L      M     KL       L  DD DETGLGC

+
                           70            80
FELV-B         FPGYGCDQPMRRWQQRNTP-------------------------------------------FYVC
FELV-B2
F-MULV          QAP  SSPPGPPCCSGGSSPGCSRDCNEPLTSLTPRCNTAWNRLKLDQVTHKSSEG
AKV            RAPFSPPPPGPPCCCSGGSSDSTPGCSRDCEEPLTSYTPRCNTAWNRLKLSKVTHHAHNGG
M-MULV         QSPFSSPPPGPPCCCSGGS-S--PGCSRDCEEPLTSLTPRCNTAWNRLKLDQTTHKSN EG
M-MCF          RTPGSRKRARTFD-------------------------------------------------

+---------C2B---------+                +-----------I21B---------+----------C4B---------
                           90           100           110           120           130           140
FELV-B         PGHANRKQ--CGGPQDGFCAVWGCETTGETYWRPTSSWDYITVKKGVTQGIYQCSGGGWC
FELV-B2
F-MULV          SHRPREAKS       DSFY     S       RA  KS           DNNL  TNQAVQVCKDNK
AKV            PHRPRWARS       ESFY     S       RAS KS           SNNL  SDQATPVCKGNE
M-MULV         PHRPRESKS       LSFY     Y       RA  KS           NNNL  SDQAVQVCKDNK
M-MCF          HTVPTG---       REY      GK      QA              R     NPR-N

+---C5B-----+        +-----------C6B-----------+       +---------C7B---------
                           150           160           170           180           190
FELV-B         GPCYD--KAVHSST-TGASEGGRCNPLILQFTQKGRQ-TSWDGPKSWGLRLYRS-GYDPIA
FELV-B2
F-MULV          W---           G        AI    NA    V     ITGHY     V      Q  GL
AKV            W---      S    ---       TIR   SF    KA    VTGHW-    V      H  GL
M-MULV         W---           ---       VIR   DA    R     TTGHY     V      Q  GL
M-MCF              SS-        ---       VIE   DA    KKA-  TTGHV     V      TI VT
                   NIK        TP
```

FIGURE 3

```
            +------C16B------C        +--------C13B--------+-------C        +--------C18B--------
                    10              20              30              40              50
FELV-B   ---EPISLTVALMLGGLTVGGIAAGVGT-GTKALIETAQFRQLQMAMHTDIQALEESISAL
FELV-B2                                    L A                       D
M-MULV   ---   V       L    L      A   I     T MA Q   Q   A VQD LREV K    N
AKV                                    M                                K    T
ATLV     AVBVAVW VS    AM AGVA     TGSMSLASG S LHE-----VDK   SQ TQA VKN

+--------C--------+--------I4B--------+--------I28B--------+--------I5B--------+--------I6B--------
                    60              70              80              90              100             110
FELV-B   EKSLTSLSEVVLQNRRGLDILFLQEGGLCAALKEECCFYADHTGLVRDNMAKLRERLKQRQ
FELV-B2                                K                                                         K
M-MULV                                                                RDS                          N
AKV                                                                                                S
ATLV     H  N LKIAQYAA       WEQ   K  QIQ R PNITNSH PI----Q   PPLEN

+--------C--------+--------I7B--------+
                    120             130             140             150             160             170
FELV-B   QLFDSQQGWFEGW-FNKSPWFTTLISSIMGPLLILLILLFGPCILNRLVQFVKDRISVVQ
FELV-A                        L-       R           T     IV  M
M-MULV   K      E              L-      R           T     IV  M
AKV                                                                      I
ATLV     RVL---T  GLN DLGL Q AREALQTGITLVAL  VI A        RQ  RHLPSRVRYPHY 180             190
FELV-B   ALILTQQYQQIKQYDPDRP--
FELV-A               R
M-MULV       V    H L PIEYEP--
AKV                    T  DCKSRE
ATLV     S   KPESSL-----------
```

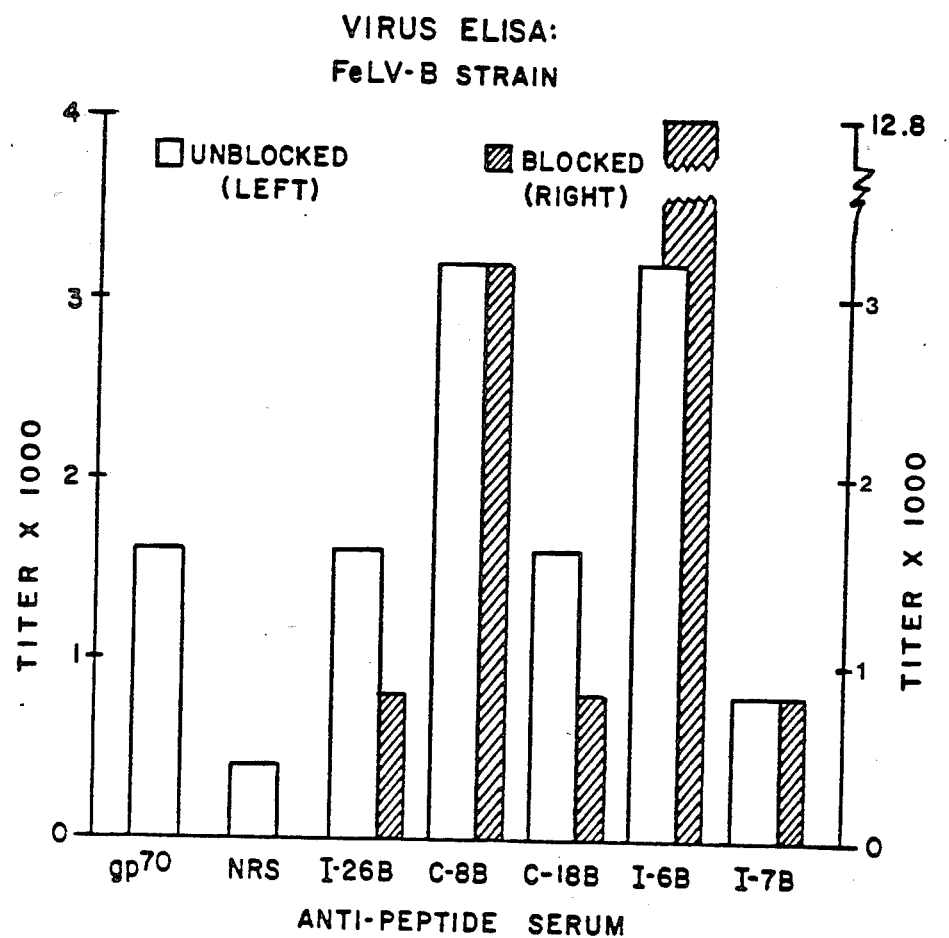

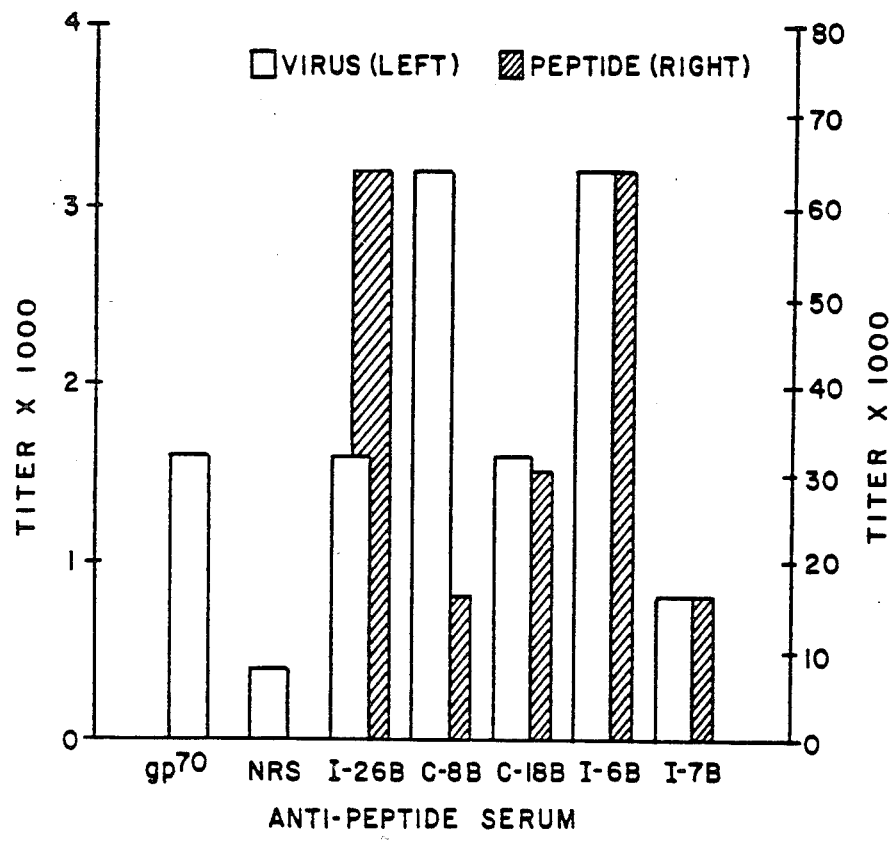

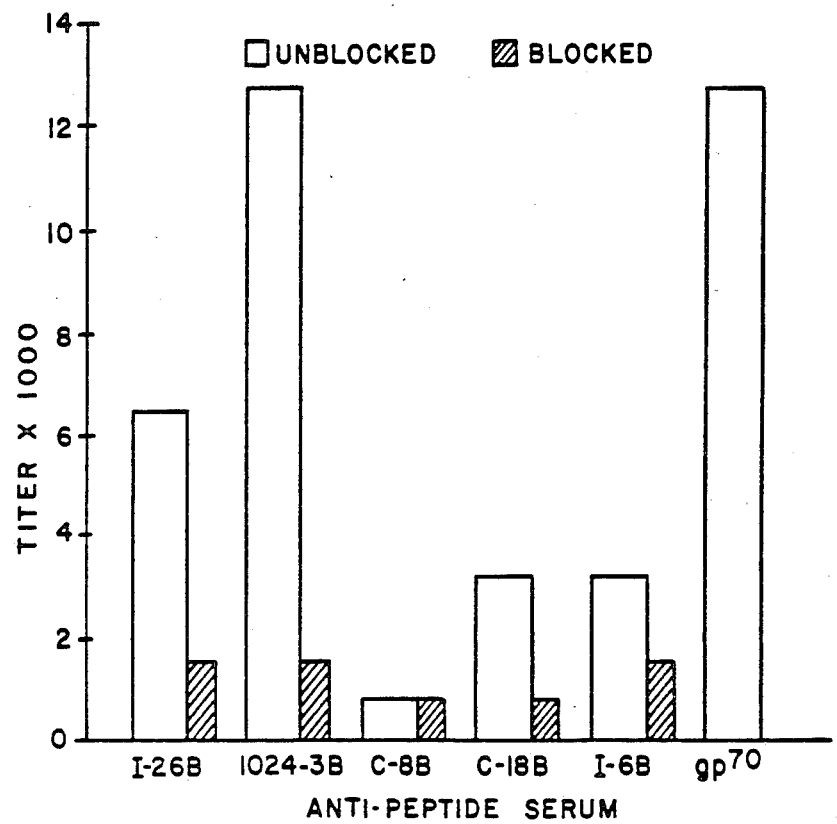

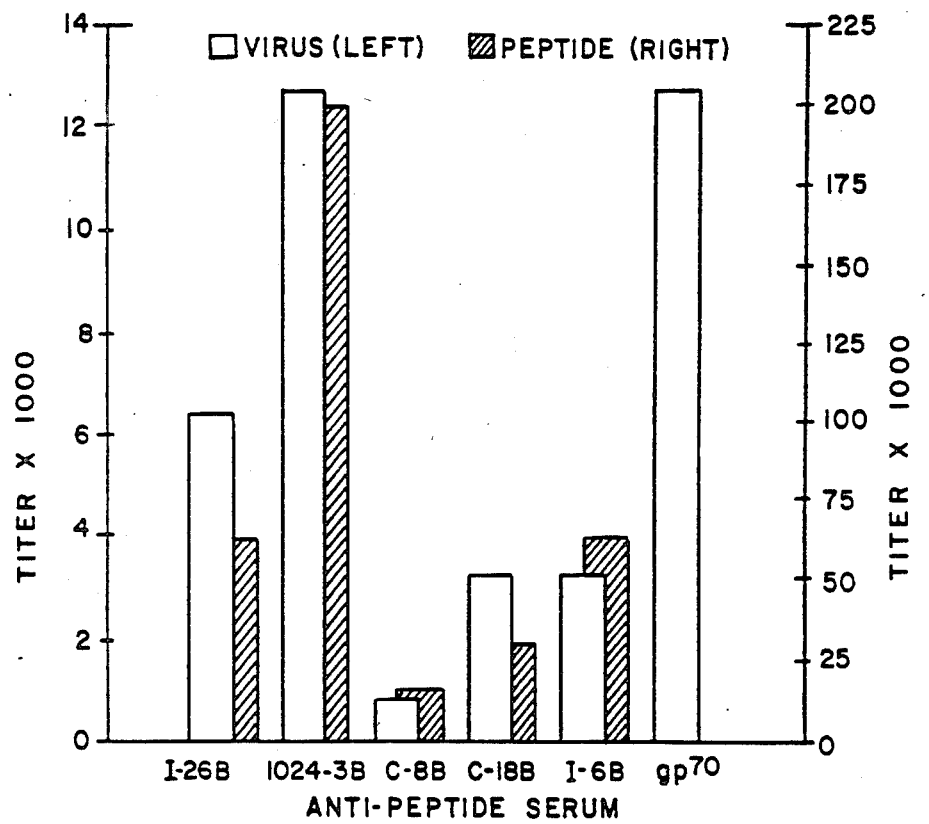

LEUKEMIA-ASSOCIATED VIRUS IMMUNOGEN, VACCINE AND ASSAY

CROSS-REFERENCE TO RELATED APPLICATION

This is a continuation-in-part of copending application Ser. No. 603,348, filed April 24, 1984, now U.S. Pat. No. 4,663,436.

TECHNICAL FIELD OF THE INVENTION

The present invention relates to vaccines and immunogens used in the detection, treatment and prevention of infections caused by leukemia-associated viruses, and particularly Feline Leukemia Virus (FeLV).

BACKGROUND OF THE INVENTION

Since the Cretaceous Period, animals have undergone great speciation and divergence. The types of viruses infecting these evolving animal species must also have been subjected to evolutionary pressures resulting in the selection of viruses that now exist. Recently, it has been found that certain leukemias in animals are associated with certain retroviruses. Though it has not been conclusively shown, it is believed that the various leukemias are caused by those retroviruses. Among the leukemia-associated viruses now known are the murine leukemia-associated viruses Murine Leukemia Virus (MuLV), Mink C 11 Focus-Forming Virus (MCF) and AKR Ecotropic Virus (AKV); feline leukemia-associated viruses such as Feline Leukemia Virus (FeLV); and human leukemia-associated viruses Human T-Cell Leukemia Virus (HTLV) and Adult T-Cell Leukemia Virus (ATLV). It has also recently been shown that ATLV and HTLV are closely related.

A recent paper reports exact amino acid sequence homologies of ten residues each among proteins that constitute the envelopes of nine leukemia-associated viruses, including (F-Friend), Moloney (M-MuLV), AKV, and Gross Murine Leukemia Viruses, Feline Leukemia Virus as well as among the envelope proteins of HTLV-I and HTLV-II. Cianciolo et al., *Nature* (London) 311:515 (1984). The recently reported genomic sequence and putative translated amino acid residue sequence of AIDS Associated Retrovirus-2 (ARV-2) indicates that that viral envelope protein contains a somewhat shorter region of close similarity (positions 776-782 from the amino-terminus of the putative protein encoded by env gene) to the homologous sequences reported by Cianciolo et al., above. Sanchez-Pescador et al., *Science* 227:484 (1985).

The leukemia-associated viruses are C-type retroviruses having their genetic information stored on RNA encased in a core which in turn is surrounded by an envelope. The strand of RNA has three genes arranged in the following order from the 5' to the 3' end: gag, pol, and env. The gag gene encodes for a nonglycosylated precursor molecule that is proteolytically processed into smaller proteins that are used to construct the core. The pol gene encodes for a protein that is proteolytically processed to form a RNA-dependent DNA polymerase (reverse transcriptase) eecessary for translating the RNA virus gene into DNA for use by the cell.

The third gene, env, is adjacent a long terminal repeat seuuence (LTR) and encodes for a polyprotein. This polyprotein is glycosylated and proteolytically processed into two smaller proteins of unequal size, the longer protein being linked by a disulfide bond to the smaller protein.

In the case of FeLV, these two envelope proteins have weights of 70 and 15 kilodaltons and are known respectively as gp70 and p15E. The larger envelope protein (e.g., gp70) is amino-terminus oriented while the smaller protein (e.g., p15E) is carboxy-terminus oriented on the polyprotein. These proteins together with a lipid membrane form the envelope protecting the virus core. The large glycosylated protein forms a knob-like structure linked by the disulfide bond to the small protein that forms a spike-like structure extending through the lipid membrane.

Exemplary of leukemia-associated viruses is the Feline Leukemia Virus (FeLV). Infections by FeLV have been extensively studied and serve as a useful model for leukemia-associated viruses. FeLV is horzzontally transferred, that is directly from cat to cat, predominantly by contact with salivary and nasal secretions through eating utensils and mutual grooming.

Within six weeks of infection with FeLV, the cat develops usually one of two major host-virus relationships. The first is a self-limiting infection (regressive infection) in which the cat develops sufficient antibodies against both the Feline Leukemia virus and lymphomas which express the feline oncornavirus-associated cell membrane antigen (FOCMA). These cats do not develop FeLV-related diseases and a short time after infection neither FeLV nor FeLV antigens can be detected in the cat's tissue.

The second major host-virus relationship is the persistant active infection (progressive infection) which generally leads to the death of the cat. Death can be caused by proliferative disorders such as lymphosarcoma and leukemia, and anti-proliferative diseases such as aplastic anemia, and secondary viral or bacterial infettions that arise because of the immunosuppression caused by FeLV. See generally Feline Leukemia, by Richard G. Olsen, CRC Press, USA. (1981).

FeLV is infectious and replicates freely in cats cells (exogenous) and has been identified as having three specific serotypes or subgroups, which have been designated as A, B, and C, based on the presence of specific virion envelope antigens. Of the three types of FeLV, serotype A designated as FeLV-A, is the most commonly isolated subgroup. FeLV-B is generally found in association with FeLV-A, and FeLV-C is relatively rare and has been isolated along with FeLV-A and FeLV-B from cats with polycythemia. Nucleic acid hybridization studies show structural homologies of at least 85 percent between the three subgruups while greater divergence is noted by T1 oligonucleotide analysis.

There have been previous attempts to prepare vaccines against Feline Leukemia virus. Unfortunately, while some of these vaccines have produced antibodies against FeLV, many not only failed to protect cats from challenge by FeLV, but when the cats were challenged, there was earlier death and larger mean tumor size in comparison with control cats that were not vaccinated. See Salerno, et al. *Proc. Soc. Exp. Biol. Med.*, 160, 18 (1979) and Nathes et al., *Cancer Res.*, 39, 950 (1979).

In more recent reports, a vaccine against *Feline Leukemia Virus* is described in U.S. Pat. No. 4,332,793. That vaccine is disclosed to utilize a neoantigen of the FOCMA-type and a FeLV virion of the gp70-type. Additionally, a glycoprotein having a molecular weight of 61,000–68,000 daltons and polypeptide portions thereof having molecular weights in excess of 42,000 daltons are reported to be found on the surfaces of cells infected with HTLV, and might be useful as immounogens in vaccines against such viruses (PCT/US 84/00561).

It would be desirable to produce a vaccine and antibodies that would provide protection against a leukemia-associated virus and the diseases it causes. Historically, vaccines and antibodies have been prepared by killing or attenuating viruses and then injecting the resulting virus particles into a patient or host animal. However, such vaccines always have the inherent threat that the virus may not be completely killed or sufficiently attenuated. The "vaccine" sometimes itself causes disease.

The threat of unattenuated viruses can sometimes be overcome by using only a portion of the virus. This portion is usually a protein from a capsid or envelope which forms the outer portion of the virus. However, even this method is not without well-known difficulties including possible pathogenic responses. The produced vaccine may include antigens that compete with or are even detrimental to the desired immune response. Other antigenic material may also be present that is unrelated to the desired immune response and can cause undesirable side effects.

Various attempts have been made to manufacture vaccines and antibodies to other diseases by other methods. These methods include producing antigen and antibody-producing cells by recombinant DNA techniques and hybridoma methods. However, these methods in addition to being relatively complicated and expensive, are time consuming and have relatively low yields both quantitatively and qualitatively. Great care must be taken in preparing the vaccine or antibody producing cell and in harvesting the desired product. There is also concern about the safety and reliability of any method that requires the desired product be separated from undesired, possibly pathogenic components.

Recently, certain pathogen-related proteins have been immunologically mimicked by a synthetic polypeptide whose sequence corresponds to that of a determinant domain of the pathogen-related protein. Such findings are reported by Sutcliffe et al., *Nature*, 287, 801–805 (1980); Lerner et al., *Proc. Natl. Acad. Sci. USA*, 78, 340–347 (1981); and Bittle et al., *Nature*, 298, 30–33 (1982). A review of the subject was reported by Sutcliffe et al., *Science*, 219:660–666 (1983). The peptide sequence of a natural protein can be determined from the protein itself or from the nucleotide sequence of the genome encoding that protein.

While the general concept of preparing synthetic antigens has been described, there remains a large area that continues to defy predictability. The field remains largely a matter of speculation, and of trial and error. The many steps needed to determine a retrovirus protein sequence from the RNA genome make it far from certain that any peptide sequence derived will have the desired immunogenic properties.

For example, the enzyme reverse transcriptase is used to polymerize nucleotides into a strand of DNA complementary to the viral RNA genome. Since about one nucleotide in five hundred is miscopied, the resulting DNA can be in error. In addition, the virus RNA molecule used to make the DNA can itself contain errors in transcription. The virus RNA was made in a living cell by RNA polymerase from DNA which in turn was made by reverse transcriptase in a similar process.

After the DNA copy has been prepared, it is then linked to a plasmid vector, a process which has been shown to often cause rearrangements in the cloned DNA fragment. The plasmid is then introduced into a bacterium, and transformed bacterial colonies carrying the recombinant plasmid are selected. A transformed colony is fragmented by streaking on a growth plate and a single isolate is picked for large scale growth and DNA preparation. Since many rounds of DNA replication have occurred in this process, one or more nucleotide-altering events can alter the gene of interest. There is no selective pressure for the bacterium to maintain the desired virus gene. A change could render the DNA sequence of such a gene meaningless or greatly lessen its utility as a blueprint for peptide sequence selection. There is no guarentee that an antigen or immunogen produced according to this sequence will have its desired biological activity.

In addition to developing a vaccine against leukemia-associated viruses, a reliable test for such leukemia-associated viruses is also needed. Generally, such tests have relied on the use of polyclonal antibodies raised to the whole or portions of a leukemia-associated virus. Unfortunately, the present tests not only give false positive results, but have also occasionally given false negative results. See *Feline Leukema supra.*, pgs. 111 and 112. In addition, some of these tests rely on immunodiffusion and immunofluorescence which can be difficult to use as well as time consuming.

Accordingly, it would be desirable to develop an immunogen that could be used as part of a vaccine for the treatment and prevention of infections caused by a leukemia-associated virus. Such an immunogen would also be useful for raising antibodies that can either be used for the treatment of leukemia-associated virus diseases or as part of an assay system for such diseases. Such an assay system should be easy to use and reliable. The present invention meets these desires.

| ABBREVIATIONS | | |
|---|---|---|
| Amino Acid | Three-Letter Abbreviation | One-letter Symbol |
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Adult T-Cell Leukemia Virus | ATLV | |
| AKR Ecotropic Virus | AKV | |
| Bovine Serum Albumin | BSA | |
| Bovine Lacto Transfer Technique Optimizer | BLOTTO | |
| Enzyme Multiplied Immunoassay Technique | (EMIT) | |

| ABBREVIATIONS -continued | |
|---|---|
| Enzyme-linked Immunosorbent Assay | (ELISA) |
| Feline Leukemia Virus | FeLV |
| Complete Freund's adjuvant | CFA |
| Incomplete Freund's adjuvant | IFA |
| Human T-Cell Leukemia Virus | HTLV |
| Keyhole Limpet Hemocyanin | KLH |
| Long Terminal Repeat | LTR |
| Mink Cell Focus-Forming Virus | MCF |
| Minimum Eagels Medium | MEM |
| Murine Leukemia Virus | MuLV |
| Normal Rabbit Serum | NRS |
| Phosphate-buffered saline | PBS |
| Radioimmune assay | RIA |

SUMMARY OF THE INVENTION

The present invention involves polypeptides with amino acid residue sequences corresponding to the sequences of antigentic determinant domains of an envelope protein of a leukemia-associated virus. For ease of description, the term peptide sequence will be used to mean amino acid residue sequence. The words "peptide" and "polypeptide" are used interchangeably herein. An antigentic determinant domain is that portion of a molecule that serves as an immunogen to stimulate antibody production, or as an antigen that binds (immunoreacts) with its corresponding antibody. The term antigen as used herein includes the definition of the term immunogen.

The polypeptide has the capacity when injected into an animal host as a conjugate of the polypeptide bound to an antigenic carrier, to act as an immunogen and induce the production of antibodies by the host. Often the polypeptide can induce the production of antibodies alone without first being bound to a carrier. The word "animal" as used refers to animals which are capable of producing antibodies. The produced antibodies immunoreact with the virus and preferably also neutralize the virus and protect the host from infection caused by the virus. Specific antigenic determinant domains of leukemia-associated virus proteins are disclosed below.

The polypeptide can be used alone or together with other components to form an immunizing composition such as a vaccine, as part of an assay system, or for the production of antibodies to a leukemia-associated virus. The antibodies either whole, or in portions including the combining sites, can be used together with an appropriate indicating means in a diagnostic assay. Since the desired polypeptide can be synthetically made in a relatively pure form, the problems with other methods of immunogen and vaccine manufacture, including co-production of competitive antigens and contaminants, are avoided.

The polypeptide of this invention preferably is about 8 to about 40, and optimally about 12 to about 20, amino acid residues in length and linked to a carrier to form a conjugate. The polypeptide can be used along with physiologically acceptable diluents such as water, saline or adjuvants to form an immunizing composition. A polymer of several such polypeptides can also be produced for increased effectiveness or to provide protection to several strains of a virus. An effective amount of the polypeptide when introduced into an animal acts as a vaccine to produce antibodies that immunoreact with the leukemia-associated virus and protect the animal from the infection by the virus. The immunizing composition can also be used to raise antibodies all or portions of which, are useful in an assay system for detecting such an infection. The antibodies can also be used in the treatment of such an infection by providing passive immunity.

Still further advantages and benefits of the present invention will become apparent to those skilled in the art from the following detailed description, examples, and claims which follow.

BRIEF DESCRIPTION OF THE DRAWINGS

FIGS. 1 and 2 show the peptide sequences of the large envelope proteins of FeLV-B, FeLV-B2, Moloney Murine Leukemia Virus (M-MuLV), Friend Murine Leukemia Virus (F-MuLV), Moloney Mink Cell Focus-Forming Virus (M-MCF) and AKV. Amino acid residues present in other proteins that are common to FeLV-B gp70 are represented by blanks in the other sequences. Dashed lines indicate deletions, which were located by manually aligning the nucleotide sequences of the viruses relative to highly conserved regions. Amino acid residue numbering is relative to the FeLV-B sequence and portions of that sequence identified by "I" and "C" designations were the peptide sequences studied. Sequence data for FIGS. 1 and 2 were obtained as follows: F-MuLV, from the peptide sequence of Chen, *Proc. Natl. Acad. Sci. (USA)* 79:5788–5792 (1982); AKV from the nucleotide sequence of Lenz et al., *J. Virol.* 42:519–529 (1982); M-MuLV from Shinnick et al., *Nature* 293:543–548 (1981); and M-MCF from Bosselman et al., *J. Virol.* 44:19–31 (1982).

FIG. 3 shows the peptide sequences of the small envelope prtteins of FeLV-B, FeLV-B2, M-MuLV, AKV, and ATLV. Only amino acid residues which differ from the FeLV p15E are shown, with deletions represented by dashed lines as above. The sequences were derived as described above with ATLV derived from Seiki et al., *Proc. Natl. Acad. Sci.* (USA), 80:3618–3622 (1983).

FIG. 4 shows a partial amino acid residue sequence of the large envelope protein of FeLV-B (gp70) from position 198 through 237 from the amino-terminus. The peptide sequences of polypeptides I26B and C8B are shown immediately above the partial gp70 sequence with their termini indicated by vertical lines. The peptide sequences of four overlap polypeptides denominated 1024–3B, 1052–13B, 1052–14B* and 1052–15B are indicated by vertically-end horizontal lines above the gp70 sequence to which they are homologous. Polpeptide 1052–14B* was prepared by omitting the arginine (R) at position 227 of gp70.

FIG. 5 is a bar graph showing the results of binding and binding inhibition ELISA determinations made using FeLV-B affixed to a microliter plate well as a solid phase-affixed antigen and various heat inactivated rabbit antisera. The antisera utilized were raised to the gp 70 protein (gp70), polypeptides I26B, C8B, C18B, I6B and I7B, using normal rabbit serum (NRS) as control. Open bars indicate use of serum without an added blocking antigen while hatched bars indicate use of a blocking antigen; i.e., the polypeptide immunogen. The ordinate is in units of one thousand times the highest titer (lowest antibody concentration) that provided a positive binding result; i.e., an absorbance at 490 nanometers that was 0.1 optical density units greater than the control. The presence of an immunoreaction (binding) was visualized by admixture of peroxidase labeled goat anti-rabbit IgG using ortho-phenylenediamine and hydrogen peroxide as the visualizing substrates, as is discussed hereinafter.

FIG. 6 is a bar graph that compares ELISA binding results of the antisera of FIG. 5 with solid phase-affixed FeLV-B virus (open bars and left ordinate) and with the immunogenic polypeptide used to raise each serum (hatched bars and right ordinate). The open bars of FIG. 6 are thus a repeat of the open bars of FIG. 5. Both ordinates are in units of titer times one thousand, with the titers being obtained as discussed in FIG. 5.

FIG. 7 is a bar graph showing the results of binding and binding inhibition ELISA determinations made using FeLV field strain as a solid phase-affixed antigen and various heat inactivated rabbit antisera. The antisera were raised to synthetic polypeptides I26B, 10243B, C8B, C18B, I6B and the gp70 protein (gp70). The results are reported as in FIG. 5.

FIG. 8 is a bar graph that compares ELISA binding results of the antisera of FIG. 7 with solid phase-affixed FeLV field strain virus (open bars and left ordinate) and with the immunogenic polypeptide used to raise each serum (hatched bars and right ordinate). The results are reported as in FIG. 6.

DETAILED DESCRIPTION OF THE INVENTION

Figure 2:
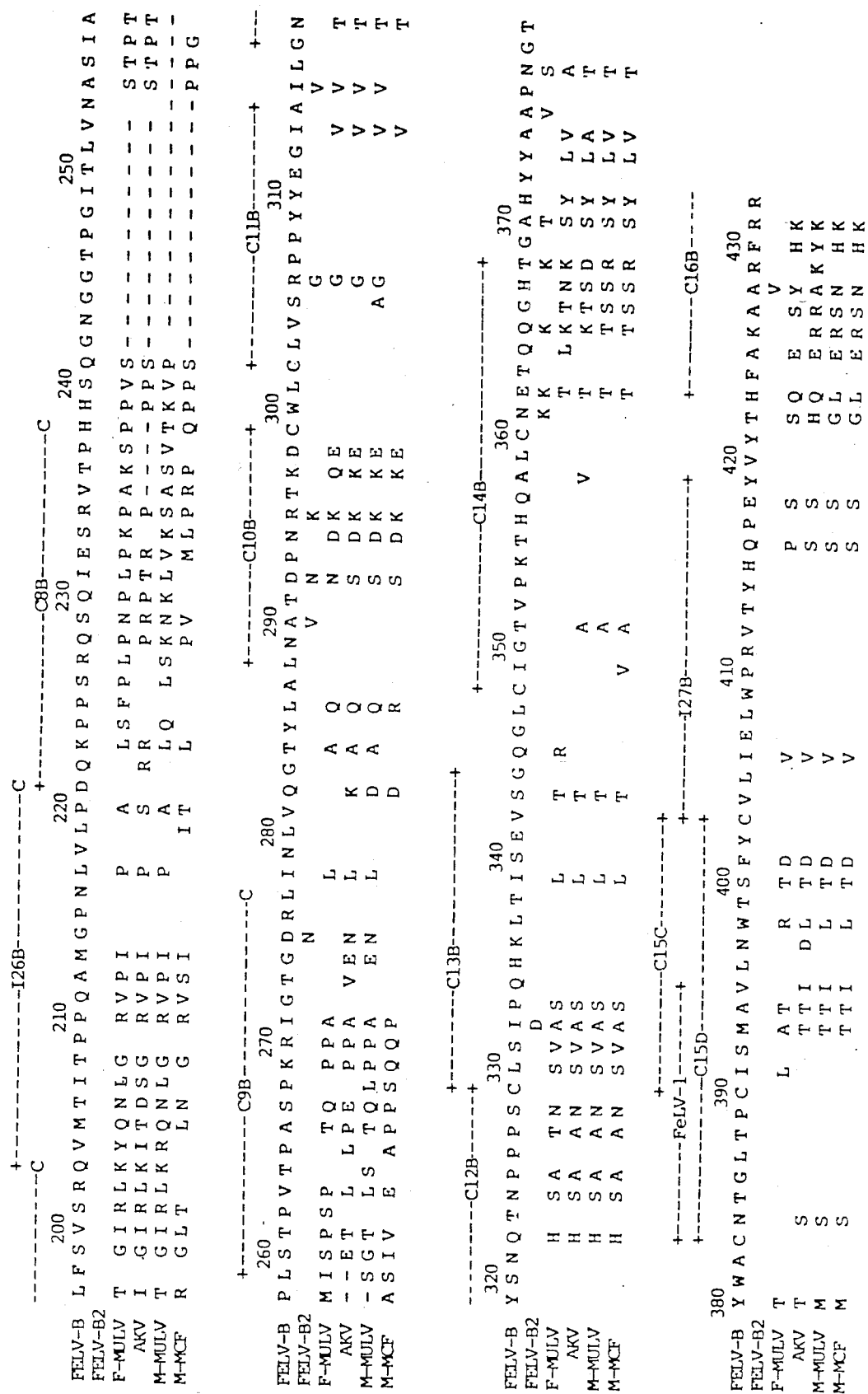

The present invention has several embodiments, each of which is related to comparatively short polypeptides that have unexpectedly been found to be immunologically active. These polypeptides either alone or as part of a conjugate induce the production of antibodies that immunoreact with antigens of leukemia-associated viruses. The polypeptides contain amino acid residues which correspond to the amino acid residues in an antigenic determinant domain of an envelope protein of a leukemia-associated virus.

In particular, the polypeptides of the present invention correspond to portions of the virus proteins which are homologous to certain portions of the FeLV-B envelope proteins gp70 and p15E. Referring to FIGS. 1 and 2 showing the large envelope proteins, the portions of the large envelope proteins of particular interest are homologous to FeLV-B gp70 from about position 45 to about position 65, about 205 to about position 240, about position 290 to about position 330, about position 345 to about position 370, and from about position 390 to about position 420 all taken from the amino-terminus of gp70. Referring to FIG. 3, the portions of the small envelope proteins of particular interest are homologous to FeLV-B p15E from about position 45 to about posttion 70 and from about position 105 to about position 150, all taken from the amino-terminus of p15E.

The FeLV-B peptide sequence from about positions 70 through about 95, and more from about particularly about positions 70 through about 80, is similar to peptide sequences of several leukemia-associated viruses, including HTLV-I, HTLV-II, and ARV-2. Cianciolo et al., above. Generally, those portions of the leukemia-associated virus envelope protein of particular interest are homologous to a portion of a FeLV-B envelope protein whose sequence corresponds to an FeLV-B polypeptide which induces the production of antibodies, having the capability of neutralizing live FeLV-B virus particles as described in more detail below.

Polypeptides which induce the production of antibodies showing greater than 25 percent neutralization in the in vitro assay described herein are preferred. The percent neutralization is determined by reacting sera containing the antibodies with live virus particles. The reacted sera and virus particles are then inoculated on live animal cell; i.e., mammal cell culture to determine the remaining infectability of the virus particles. Control serum collected from the animal prior to inoculation with the polypeptide is also reacted with the live virus particles and provides a base reference to determine percent neutralization.

The type of live animal cell used varies depending on the leukemia-associated virus being investigated. As discussed in more detail below, dog thymus cells, in particular cell line Cf2th, can be used for feline leukemia-associated viruses. Other suitable cells or various leukemia-associated viruses can be determined by reference to the American Type Culture Collection Catologue of Strains II, 4th Ed. (1983). In the case of human leukemia-associated viruses, human cord blood T-cells can be used. See Manzari et al., *Proc. Natl. Acad. Sci. U.S.A.*, 80:11-15 (1983).

The polypeptides of the present invention can be used alone or together with other components to produce antibodies, as part of an assay system, or to produce an immunizing composition such as a vaccine. Polypeptides of the present invention can also be formed into polymers to induce the production of antibodies which immunoreact with more than one strain of leukemia-associated virus. The antibodies raised to the polypeptides can be used in assay systems for treating infections of leukemia-associated viruses.

I. THE LEUKEMIA-ASSOCIATED VIRUS PROTEINS

The choice of the polypeptide utilized for the present invention begins with the peptide sequence of the envelope proteins of a leukemia-associated virus. The peptide sequence may be determined by several techniques well-known in the art such as the classical, wet chemical technique of partial hydrolysis and sequencing of the individual products. The more recent techniques of sequencing of the genome from the virus and of translating that genomic sequence into its corresponding protein sequences has been used as described below.

Determination of Envelope Peptide Sequences

Previously, the peptide sequences of the envelope proteins of Gardner-Arnstein FeLV-B (GA-FeLV-B) and FeLV-B2 (another strain of FeLV-B) had not been determined. For ease of description "FeLV-B" is used to identify Gardner-Arnstein FeLV-B while FeLV-B2 is used to identify the second (otherwise unnamed) strain studied. Peptide sequences for the other leukemia-associated viruses were derived from the publications cited before. The sequence of FeLV-B2 was determined using the procedures for FeLV-B described below except for the virus analyzed. The determination of the FeLV-B peptide sequence discussed below can be considered exemplary of leukemia-associated viruses. See also, Elder et al., *J. Virol.* 46:871-880 (1983).

Clones. A recombinant DNA clone (designated pFGB) of an infectious clone of Gardner-Arnstein FeLV-B provirus in the plasmid pBR322 was utilized for these studies. The plasmid was cloned from the lambda HF60 isolate that was obtained from a Charon 4A library of Eco R1 cleaved DNA from GA-FeLV-B infected human RD cells. See Mullins et al., *J. Virol.* 38:688-703 (1981). The lambda HF60 insert was cloned into the Eco R1 site of pBR322. Subcloning was performed on this plasmid utilizing a Hind III site in the 3' portion of the pol gene and another Hind III site outside of the integrate virus within cellular flanking sequences. Ligation of pBR322 at the Hind III site yielded two plasmids, one containing a 6.5 kilobase insert comprising the 5' portion of the transcribed viral gene, and another (pFGB3.5) that contained the envelope gene as well as the 3' long terminal rppeat (LTR) of the transcribed viral genome. The pFGB3.5 clone was utilized for sequence analysis.

Isolation of recombinant DNA. A modification of the boiling procedure of Holmes and Quigley was used to purify the plasmid DNA. See Holmes et al., *Anal. Biochem.* 114:193-197 (1981) and Sparks and Elder *Anal. Biochem* 135:345-348 (1983). *E. coli* C600 cells were transformed with pFGB3.5 and colonies resistant to ampicillin and sensitive to tetracycline were selected. An overnight culture was grown from a single colony in yeast-tryptone medium from Difco Laboratories of Detroit, Michigan in the presence of ampicillin (33 microgram micrograms/milliliters). One liter cultures of yeast-tryptone medium plus ampicillin were then inoculated with 5 milliliters overnight culture and allowed to grow at 37 degrees C. until an optical density at 550 nanometers (18,182 cm$^{-1}$) of 0.6 was attained. Chloramphenicol (0.173 grams/liter) was then added, and the cultures were amplified overnight at 37 degrees C. with vigorous agitation.

Cells were then harvested, washed once with M9 medium (6 grams $Na_2HPO_4$, 3 grams $KH_2PO_4$, 0.5 grams NaCl in 1 liter $H_2O$) and resuspended in lysis buffer (0.05 molar Tris, pH 7.8; 0.05 molar EDTA, 1 percent polyoxyethylene (9) octyl phenyl ether, 8 percent sucrose). Lysozyme (15 milligrams/milliliter final concentration) was added to the resuspended cells. The suspension was placed in a beaker and boiled for approximately 30 seconds, at which time a clot formed. The clot-containing suspension was centrifuged at 100,000×g for 1 hour to remove chromosomal DNA and associated proteins. Sodium acetate was added to the sueernatant to provide a 0.4 molar (M) concentration and an equal volume of iso-propanol was added to provide a precipitate that was recovered. The recovered precipitate was redissolved in 4 milliliters of water, the sllt concentration adjusted to 0.4M sodium acetate and 2.5 volumes of ethanol were added to form a second precipitate.

The second precipitate was dissolved in 10 milliliters water and the majority of protein and associated ribosomal RNA was precipitated by the addition of 40 milliliters saturated ammonium sulfate. After 1 hour at 4 degrees C., the third precipitate so formed was removed by centrifugation and the supernatant was passed over a column (Bio-rad Laboratories, Inc., of Richmond, California, 1.5×20 cm.) containing 5 grams preparative C18 silca beads (50-200 microns, Waters Associates Inc. of Milford, Massachusetts) which had been pretreated with 100 percent methanol and equilibrated in deaerated water. The column was washed with 10 milliliters water and plasmid DNA and contaminating RNA were then eluted with 30 percent methanol in water.

Plasmid DNA so recovered was virtually 100 percent supercoiled and free of chromosomal DNA. RNA which comprised 30-50 percent of the recovered nucleic acid could be removed by RNase treatment, but did not interfere with sequence analysis. pFGB3.5 amplified well and approximately 15 milligrams plasmid DNA/liter were recovered by this technique. Variability in recoveries with various plasmids proved to be a function of amplification and not of the experimental protocol.

DNA sequencing. DNA sequencing of FeLV-B and FeLV-B2 was performed essentially as described by the technique reported by Maxam and Gilbert, *Enzymol.* 65:499-560 (1980) except that 4 percent formic acid was used in place of 4 percent pyridinium formate for the adenine plus guanine reaction.

Defining the envelope gene. The envelope gene env resides at the 3' end of the FeLV genome and is translated from a spliced mRNA as a polyprotein. This polyprotein is proteolytically processed into the large envelope protein gp70 and the small envelope protein p15E during virus maturation. Tentative locations for the amino-terminus of these proteins were assigned by aligning the deduced peptide sequence from a large open reading frame of the sequence with the peptide sequences of Rauscher and Friend virus large envelope proteins.

As for the other retroviruses studied, a long open reading frame is present in FeLV-B and FeLV-B2, which when translated into amino acid residues, shows sufficient homology with previously published sequences so as to facilitate tentative location of the gene products, gp70 and p15E. As with Moloney (M-MuLV), and AKR ecotropic virus (AKV), the coding sequence for the envelope gene is in a different reading frame from the polymerase gene, which precedes it to the 5' side.

By alignment with the murine sequences, the amino-terminus of p15E is at nucleotide 1,457, which dictates a gp70 molecule 432 amino acid residues long and a p15E molecule comprising 197 amino acid residues. The precise location for processing of the polyprotein or whether amino acid residues are removed during processing is unknown for FeLV-B. However, the amino acid sequence data of Chen (supra) with the Friend virus large envelope protein indicates that a single cut is made prior to the amino-terminus of p15E, with no amino acids removed. Similar cleavage is believed to also take place in ATLV.

The correlations between the various retrovirus peptide sequences shown were determined by manually aligning the peptide sequences and providing for deletions and additions where appropriate. The various sequences together with their respective homologies are shown in FIGS. 1-3.

Comparative analysis of the large envelope proteins

Comparison of the amino acid sequences of the large envelope proteins in FIGS. 1 and 2 yields considerable insight into which regions of the large envelope protein are conserved as well as which regions are specific for a given virus or host range group. The large envelope proteins of FeLV-B and FeLV-B2 are 432 amino acid residues long compared to 312 for ATLV, 445 for (F-MuLV), 439 for AKV, 436 for M-MuLV, and 407 for a M-MCF. The FeLV-B large envelope protein contains 12 possible glycosylation sites (Asn-X Thr/Ser), compared to 4 for ATLV, 7 for F-MuLV, 7 for AKV, 7 for M-MuLV, and 7 for M-MCF. In general, the greatest degree of conservation is in the carboxy-terminal one-third of the large envelope proteins, starting at about position 270 from the amino-terminus as measured with respect to the FeLV-B peptide sequence shown in FIGS. 1 and 2.

For ease of description, the number location of amino acid residues in the peptide sequences are all identified with respect to their homologies to the FeLV-B sequence. The amino acid residue numbers are shown immediately above the FeLV-B sequence. A portion of a protein is considered homologous to portion of another protein when the two portions have the same relative locations within their respective proteins taking into acount any deletions. Thus, for example, a portion of the M-MCF large envelope protein having the peptide sequence, from left to right and in the direction from amino-terminus to carboxy-terminus, SEVTGQGLCVG is homologous to the FeLV-B large envelope protein gp70 from position 340 to position 350. At this location, the FeLV-B large envelope protein gp70 has the sequence SEVSGQGLCIG.

In this same portion of the large envelope proteins, FeLV-B2 is identical to FeLV-B, and for purposes herein is also considered homologous with FeLV-B, as is FeLV-B homologous with itself over that same portion. Thus, reference to a portion of a leukemia-associated virus protein which is homologous to FeLV over a certain range, includes not only other viruses such as MuLV or ATLV, but also FeLV-B itself.

Those portions of the respective proteins that show good correlations between the amino acid residues themselves as well as between locations of such structural affecting features as cysteine residues and hydrophilic and hydrophobic segments are believed to indicate structural similarities between the respective proteins. Generally, those portions of a protein found to be antigenic are believed to be on the outside of the protein and are therefore available for immunoreaction with an antibody.

Thus, a portion of one envelope protein exhibiting antigenic properties indicates that the homologous portion of a protein from another leukemia-associated virus should have similar antigenic properties. Using the peptide sequence of one particular leukemia-associated virus protein as a reference, other useful peptide sequences can be determined for the other leukemia-associated viruses. For further discussions regarding the antigenicity of polypeptides corresponding to homologous portions of proteins from different viruses, see International Publication WO 83/03547 published on October 27, 1983, Synthetic Picornavirus Antigen to Bittle et al; Sen et al., *Proc. Natl. Acad. Sci. U.S.A.*, 80:1246-1250 (1983); and Sutcliffe et al., supra.

The carboxy-terminal portions of the large envelope proteins are highly variable, although many of the changes are conserved (i.e., lysine for arginine) and hydrophobic and hdrophilic residues showing homologies suggesting similar structures. All the large envelope proteins shown in FIGS. 1 and 2 possess two basic amino acids just prior to the small envelope proteins which would be susceptible to a trypsin-like cleavage. As stated above, results with Friend MuLV indicate that a single cut produces the large and small envelope proteins. The amino-terminal one-third of the FeLV gp70 (position 1 to about position 160) is more closely related to the endogenous murine virus large envelope protein (presumably xenotropic) involved in recombination to form the MCF virus (M-MCF). Over this same region, F-MuLV, M-MuLV and AKV show closer relationships with each other than with FeLV or MCF.

Comparative analysis of the small envelope proteins

A comparative analysis of the predicted peptide sequences of M-MuLV, AKV, ATLV, FeLV-B and FeLV-B2 small envelope proteins are shown in FIG. 3. The M-MCF small envelope protein is inherited from the parental M-MuLV and is thus omitted. Overall, the structure of the small envelope protein is highly conserved, with 180 of 199 residues identical between M-MuLV and AKV; 154 of 199 between M-MuLV and FeLV-B p15E; 161 of 199 residues identical between AKV and FeLV-B and 52 residues identical between ATLV and FeLV-B. The identity of residues among nine small envelope viral proteins in the region that corresponds to about positions 70 through about 80 of FeLV-B and the general similarity among those proteins from about position 80 through position 95 of FeLV-B have already been noted.

The similarities in apparent structures of the small envelope proteins can also be seen by correlation of cysteine residues at positions 86, 93 and 161 as well as the respective hydrophobic and hydrophilic portions of each protein. In this regard, the leucine-residue-rich segment appearing from about position 150 to about position 157 near the carboxy-terminus is particularly hydrophobic and believed to form part of an alpha-helical structure which traverses the lipid membrane of the virus. Even though there is less direct correlation between the ATLV small envelope protein sequence and the other small envelope protein sequences, the respective proteins are nevertheless believed to be structurally similar.

As with the large envelope protein, the small envelope protein shows more structural divergence toward the amino-terminus end of the molecule. By analogy to the M-MuLV small envelope protein, the carboxy-terminus of FeLV and ATLV appears to be the leucine residue at position 180 of FIG. 3. As in the murine viruses, processing at this point yields a protein about 180 residues long with a small piece removed from the carboxy-terminus of the polyprotein. The peptide sequences of the small envelope proeeins studied except ATLV contain a single Asn-X-Ser/Thr site that could function as a siee for N-linked glycosylation. However, no carbohydrate has been detected on either murine or feline small envelope proteins.

II. THE POLYPEPTIDES

Selection of peptide sequences for synthesis

After the peptide sequences of the leukemia-associated virus envelope proteins are determined, an antigenic determinant domain that is preferably about 8 to about 40 and more preferably about 12 to about 20 amino acid residues long is then selected from the overall protein sequence. A polypeptide corresponding to the selected domain is then synthetized preferably by the solid-phase synthetic methods discussed below.

Hydrophilic domains of the envelope proteins are likely exposed on the outer surface of the virus thereby permitting good contact between an induced antibody and the virus. It is therefore preferable that the selected peptide sequence contain hydrophilic amino acid residues such as arginine, lysine, aspartic acid, glutamic acid and histidine. Selection of a hydrophilic peptide domain also provides a polypeptide that is water-soluble. It is also preferable to select a determinant domain sequence between hydrophobic residues. Hydrophobic residues are often buried within the native protein while the selected, relatively hydrophilic determinant domain between hydrophobic residues is exposed.

One or more additional amino acid residues may be added to the amino- or carboxy-termini of the synthetic polypeptide to assist in binding the synthetic polypeptide to a carrier to form a conjugate. Cysteine residues, usually added at the carboxy-terminus of the polypeptide, have been found to be particularly useful for forming conjugates via disulfide bonds, but other methods well-known in the art for preparing conjugates may be used. Exemplary binding procedures include the use of dialdehydes such as glutaraldehyde, or the use of carbodiimide technology as in the use of a water-soluble carbodiimide, e.g., 1-ethyl-3-(3-dimethylaminopropyl) carbodiimide.

Conjugate-forming antigenic carriers are generally proteins themselves and are well-known in the art. Exemplary of such carriers are keyhole limpet hemocyanin (KLH), albumins such as bovine serum albumin (BSA), tetanus toxoid, soybean agglutinin, peanut agglutinin, edestin, pumpkin seed protein as well as polyamino acids such as poly(D-lysine:D-glutamic acid). In each instance, the polypeptide of this invention functions as the specific antigenic determinant.

It is often beneficial to bind the synthetic polypeptide to its carrier by means of an intermediate, linking group as is also well-known in the art. As noted above, glutaraldehyde is one such linking group, while when a cysteine residue is present at one terminus, the intermediate linking group is preferably a N-maleimidobenzoyl N-hydroxysuccinimide ester (MBS). See generally Lieu et al., *Biochemistry* 18:690–697 (1979).

In another method, MBS is typically first added to the carrier by an ester-amide interchange reaction followed by addition of a blocked mercapto group such as thioacetic acid [CH$_3$C(O)SH] across the maleimidodouble bond. Cleavage of the blocking group follows, and then the disulfide bond is formed between the deblocked linking group mercaptan and the mercaptan of the cysteine residue of the polypeptide.

Polypeptide Synthesis and Coupling

Polypeptides of this invention can be made using known procedures and are preferably chemically synthesized. See, for example, Marglin, A. and Merrifield, R. B., *Ann. Rev. Biochem.*, 39:841–866 (1970). Generally, an immunogen or synthetic polypeptide is made by the steps of providing a plurality of amino acids which correspond to the amino acid residues in antigenic determinant domain of an envelope protein of a leukemia-associated virus and synthesizing those amino acids into a polypeptide which has a peptide sequence corresponding to the peptide sequence of the antigenic determinant domain of the envelope protein. The produced synthetic polypeptide can be used to produce a vaccine usually by linking it to a carrier to form a conjugate and then dispersing the conjugate in a physiologically tolerable diluent.

The polypeptides are preferably synthesized by the solid phase method using a cysteine resin according to previously described methodology. See Merrifield, *J. Am. Chem. Soc.*, 85, 2149–2154 (1980) and Houghten et al., *Int. J. Pep. Prot. Res.*, 16, 311–320 (1980). The side chains on individual amino aacids are protected as follows: Arg-tosyl; Ser-, Thr-, Glu- and Asp-O-benzyl; Tyr-O-bromobenzyloxy carbamyl; Trp-N-formyl. The N-formyl group on the Trp residues is removed after cleavage of the peptide from the resin support by treatment with 1.0 molar ammonium bicarbonate at a peptide concentration of 1.0 milligram/milliliter for 16 hours at the room temperature. Yamashiro et al., *J. Org. Chem.*, 38, 2594–2597 (1973). The efficiency of coupling at each step can be monitored with ninhydrin or picric acid and is preferably greater than 99 percent in all cases. See Gisin, *Anal. Chem. Aeta*, 58, 248–249 (1972) and Kaiser, *Anal. Biochem.*, 34, 595–598 (1980).

As use herein, the term "synthetic polypeptide" means a chemically, as opposed to biologically, derived chain of amino acid residues that is free of naturally occuring proteins.

It has been found that synthetic polypeptides containing between about 8 and about 40 and preferably about 12 to about 20 amino acid residues corresponding to the sequence of portions of leukemia-associated virus envelope proteins induce the production of antibodies that react with (bind to) the virus, and neutralize the virus in in vitro determinations in animal cells. Binding of antibodies to a virus is thought to be a first step in in vivo protection of an animal host by a humoral or cellular immune response. In vitro neutralization, depending upon the technique utilized, can be correlated to in vivo host protection.

Polypeptides which correspond to the sequences of several different portions of the envelope proteins have been found to induce the production of antibodies which neutralize a leukemia-associated virus. Neutralizing antibodies in sera at a 1:20 dilution which neutralize in excess of 25 percent can be obtained by using polypeptides corresponding to at least portions of the peptide sequence of FeLV-B from about position 45 to about position 65, about position 205 to about position 240, about position 290 to about position 315, about position 345 to about position 370, and about position 390 to about position 420 of the large envelope protein, as well as from about position 45 to about position 70 and about 105 to about position 150 of the small envelope protein. These sequences are identified as I10B, I26B, C8B, C10B, C11B, C14B, C15C, I27B, C18B, I6B, and I7B in FIGS. 1–3.

While the sequence designated as C15D also showed neutralization, this is believed to be due to the carboxy-terminal end portion duplicated by C15C. The amino-terminal portion of C15D is duplicated by the polypeptide identified as FeLV-1 which showed no neutralization. As discussed below, other polypeptides showed neutralization of FeLV-B, however, the portions of the envelope proteins just described are preferred.

The in vitro neutralizing antibodies having greatest ability to abrogate virus infections are produced by polypeptides corresponding to the peptide sequence FeLV-B from about position 45 to about position 65, and about position 345 to about position 370 of the large envelope protein, as well as from about position 45 to about posiiion 70 and about position 105 to about position 120 and about position 120 to about 145 of the small envelope protein p15E of FeLV-B. These sequences are identified as I10B, C14B, C18B, I6B, and I7B on FIGS. 1–3. These antibodies in sera at a 1:20 dilution neutralize live virus particles in excess of 50 percent.

Antisera raised to polypeptide I26B (positions 203–220) originally exhibited good neutralization, but the control serum also exhibited a relatively high neutralization value, thereby providing an ambiguous result. Further studies with peptide I26B and its adjacent peptide, C8B (positions 221–237), have exhibited improved results, as are shown hereinafter in Tables VI and VII.

A recent report by Nenberg et al., *Pro. Natl. Acad. Sci., USA*, 81:3675–3679 (June 1984) indicates that a monoclonal antibody denominated mAb cl. 25 binds to positions 213–226 of the gp70 molecule of Gardner-Arnstein FeLV-B. That monoclonal antibody was also reported to neutralize several FeLV strains in an in vitro focus-induction assay.

Still another polypeptide has been found which does not neutralize FeLV-B in vitro, but whose antiserum readily immunoreacts with FeLV-B and is useful to produce antibodies for an assay system. This peptide sequence is identified as C12B in FIG. 2 and corresponds to about position 315 to about position 330 of the large envelope protein gp70. This polypeptide may also be useful for providing protection to an animal through cellular responses.

Peptide I4B and it overlapping peptide I28B of p15E that correspond to positions 72 through 93 from the amino-terminus are in the region of great peptide sequence homology among several leukemia viruses. As shown in Table 1 hereinafter, antiserum raised peptide I4B exhibited neutralization of FeLV in the in vitro assay.

The region of the small envelope protein from about position 105 to about position 150 and more preferably to about position 145 of the small envelope protein with respect to FeLV-B is particularly antigenic. This portion of the FeLV-B small envelope protein p15E includes the polypeptides designated I6B and I7B. Accordingly, it is believed that any appropriately selected polypeptide corresponding to that portion of a small envelope protein taken from about poiition 105 to about position 150 would also be antigenic.

This portion of the small envelope protein can also be identified by its location between a segment centered about position 103 which is about 10 amino acid residues on the carboxy-terminus side of 2 cysteine residues spaced about 7 residues apart and located at positions 86 and 93, and the leucine-residue-rich segment at positions 148 through 157. Similarly, this region can also be described as the 50 amino acid residues on the amino-terminus side of the leucine-residue-rich segment of the small envelope protein. The term leucine-residue-rich segment refers to a segment of the small envelope protein having about 10 amino acid residues, the majority of which are either leucine or isoleucine.

Because of the relatively close correlation between tee various leukemia-associated virus proteins, it is possible to determine potential amino acid residue substitutions in the above polypeptides to correlate between FeLV-B, FeLV-B2, F-MuLV, AKV, M-MuLV and M-McF. This provides preferred peptide sequences and substitutions that correspond to one of the formulas set forth below:
(1) CDIIGNTWNPSDQEPFPGYG
(2) CI(V)GT(A)VPKTHQA(V)LCN(K) E(K or T)TQ(L)Q(K or T)G(T or S) H(N or S)T(K or D or R)
(3) GN(T)YSNQ(H)TN(S)P(A)PP(T or A)S(N)C
(4) T(D)DI(L)Q(R or K)A(E)L(V) E(D)E(K)SIS(-T)A(N)LEKSLTSLSE
(5) AKLRER(K)LK(N or S)QRQQ(K)LF
(6) D(E)SQ(T)QGWFEGW(L)FNK(R)SPWFT-TLISS(T)
(7) Q(K)V(Y or I or R)M(Q or T or L)T(N or D)I (L or S)T(G)PP(R)Q(V)A(P or S) M(I)GPNL(P)V-L(I)P(A or S or T)D
(8) DQ(R)K(L or R)P(S or Q)P(F)S(P or L) R(L or S)Q(P or K)S(N or R or V)Q (P or K)I(L or T)E(P or R or V or M)S (K or L)R(P or S)V(A or R)T(K or S or P) V(A or R)T(K or S or P)P(S or V)H (P or T or Q)
(9) RRGLDILFF(W)Q(K or E)E(Q)GGL
(10) Q(K or E)E(Q)GGLCA(K)ALK(Q)E(I)E(Q)C
wherein each amino acid residue in parentheses may independently replace the immediately previous amino acid residue; i.e., the amino acid residue immediately toward the amino-terminus, and wherein each sequence is taken from left to right and in the direction from amino-terminus to carboxy-terminus.

More preferred polypeptides and substitutions that relate to FeLV-B and FeLV-B2 have squences that correspond substantially to those set forth below, wherein the parenthesized amino acid residues and the peptide sequence orientations are as described above:
(1) CDIIGNTWNPSDQEPFPGYG
(2) CIGTVPKTHQALCN(K)E(K)TQQ(K)GHT(K)
(3) GNYSNQTNPPPSC
(4) TDIQALE(D)ESISALEKSLTSLSE
(5) AKLRER(K)LKQRQQLF
(6) DSQQGWFEGWFNKSPWFTTLISS
(7) QVMTITPPQAMGPNLVLP
(8) DQKPPSRQSQIESRVTP
(9) RRGLDILFLQEGGLC
(10) QEGGLCAALEEC The polypeptides relating to FeLV-B and identified as I10B, C14B, C12B, C18B, I6B, I7B, I26B, C8B, I4B and I28B respectively, are:
(1) CDIIGNTWNPSDQEPFPGYG
(2) CIGTVPKTHQALCNETQQGHT
(3) GNYSNQTNPPPSC
(4) TDIQALEESISALEKSLTSLSE
(5) AKLRERLKQRQQLF
(6) DSQQGWFEGWFNKSPWFTTLISS
(7) QVMTITPPQAMGPNLVLP
(8) DQKPPSRQSQIESRVTP
(9) RRGLDILFLQEGGLC
(10) QEGGLCAALEECQIGGLCAALKEEC The amino-terminus of the polypeptide sequences listed above can be any suitable terminal group such as hydrogen, an alkyl group, a cysteine residue, or an oligopeptide of not more than 50 amino acid residues that does not provide immunosuppression to the polypeptide as a whole. The carboxy-terminus of the polypeptides can be any suitable terminal group such as hydroxyl, a cysteine residue, or an oligopeptide of not more than about 50 amino acid residues that does not provide immunosuppression to theppolypeptide as a whole. Generally, where the polypeptide sequence listed does not terminate at either end with a cysteine residue, the addition of a cysteine residue to either the amino-terminus or to the carboxy-terminus is desirable to allow for linking to a carrier to form a conjugate. It is to be understood that since the polypeptides of this invention can be utilized as immunogens the presence of additional peptide sequences that provide immunosuppresion at either terminus or in an inoculum such as a vaccine is contrary to the intent of the invention. Thus, an enumerated polypeptide of this invention is free from immunosuppresive peptide sequences when another peptide sequence is also present.

The term "corresponds substantially" in its various grammatical forms as used in relation to peptide sequences means the peptide sequence described plus or minus up to three amino acid residues at either or both of the amino- and carboxy-termini and containing only conservative substitutions in particular amino acid residues along the polypeptide sequence.

The term "corresponds" in its various grammatical forms as use in relation to peptide sequences means the peptide sequence described plus or minus up to three amino acid residues at either or both of the amino- and carboxy-termini and containing conservative as well as radical substitutions in particular amino acid residues and also containing deletions or additions of particular amino acid residues along the peptide sequence.

The term "conservative substitution" as used above denotes that one amino acid residue has been replaced by another, biologically similar residue. Examples of conservative substitutions include the substitution of one hydrophobic residue such as isoleucine, valine, leucine or methionine for another, or the substitution of one polar residue for another of like charge or functonal group such as between arginine and lysine, between glutamic and aspartic or between glutamine and asparagine and the like. The term "conservative substitution" also includes the use of a substituted amino acid in place of an unsubstituted parent amino acid provided that antibodies raised to such a polypeptide also immunoreact with the corresponding polypeptide having the unsubstituted amino acid. The term "immunoreact" in its various forms means binding between a ligand such as an antigen and an antibody combining site which may be a portion of or a whole antibody.

The replacement of an ionic residue by an oppositely charged ionic residue such as aspartic acid by lysine has, on occasion, been termed conservative in the art because those ionic groups are thought to merely provide solubility assistance. However, since the replacements discussed herein are on relatively short antigens, as compared to a whole protein, replacement of an ionic residue by one of opposite charge is considered to be radical substitution as are replacements between non-ionic and ionic residues, and bulky residues such as phenylalanine, tyrosine or typtophan and less bulky residues such as glycine, isoleucine and valine.

The terms "nonionic" and "ionic" residues are used in their usual sense to mean those amino acid residues that normally either bear no charge or normally bear a charge, respectively, at physiological pH values. Exemplary nonionic residues include threonine and glycine, while exemplary ionic residues include arginine and aspartic acid.

Immunizations

The polypeptides of this invention can be used alone in straight chain or cyclic ring form, as a polymer wherein adjacent polypeptide repeating units are bonded together by oxidized cysteine residues, dialdehydes such as glutaraldehyde and the like, or as a conjugate linked to an antigenic carrier. When introduced into an animal host in a unit dose vaccine having an effective amount of polypeptide, the polypeptides are typically capable of inducing production of antibodies in the host that immunoreact with the related leukemia-associated virus. Immunizing compositions containing preferred polypeptides induce the production of antibodies that neutralize the related leukemia-associated virus in vitro as discussed hereinafter, while particularly preferred polypeptides in such compositions protect a host animal from infection caused by that leukemia-associated virus.

The "effective amount" of antigenic polypeptide in a unit dose depends upon a number of factors. Included among those factors are the body weight of the animal immunized, the carrier when used, the adjuvant when used, and the number of inoculations desired to be used. Individual inoculations typically contain about 10 micrograms to about 500 milligrams of polypeptide per kilogram body weight exclusive of any carrier to which the polypeptide may be linked. Inoculation methods and amounts in rabbits for the purpose of raising antibodies are described below.

Vaccines containing effective amounts of the polypeptide induce production of antibodies in a sufficient amount to protect the animal from infection with the respective leukemia-associated virus. The immunizing composition or vaccine can be administered intravenously using known methods. Booster injections can be given if needed. Exact doses depend on the animal and polypeptide used and can be determined using known challenge techniques. Typical amounts of polypeptide and carrier, and the specific reaction conditions for the conjugation reaction and vaccine preparation are given in Bittle et al., *Nature,* 298, 30–33 (July, 1982).

The polypeptides of the present invention can be connected together to form an antigenic polymer comprising a plurality of the polypeptides. Such a polymer has the advantages of increased immunological reaction and where different polypeptides are used to make up the polymer, the additional ability to induce antibodies that immunoreact with several different types or serotypes of a virus.

A low molecular weight polymer can be prepared by synthesizing the polypeptides as discussed above and adding cysteine residues at both the amino- and carboxy-termini to form DiCys polypeptide. Thereafter, 10 milligrams of the DiCys polypeptide (containing cysteine residues in un-oxidized form) are dissolved in 250 milliliters of 0.1 molar ammonium bicarbonate buffer in a beaker. The dissolved diCys polypeptide is then air oxidized by stirring the resulting solution gently over a period of about 18 hours. See Ellman, *Arch. Biochem. Biophys.,* 82:70–77 (1959).

The use of glutaraldehyde to form polymeric proteins and polypeptides is well known in the art and need not be discussed in detail herein.

Antibody Combining Sites

Antibody combining sites raised to or indued by the polypeptides of the present invention can be used in assays or to treat leukemia-associated virus infections. The antibodies can be used directly as whole intact antibodies or may be processed to provide Fab or F(ab')2 portions, all of which have biologically active antibody combining sites. The term "antibody combining site" indicates an antibody or the idotype-containing polyamide portion of the antibody which is biochemically active to bind with its respective antigenic ligand.

To manufacture antibody combining sites, the immunizing compositions described above can be injected into a host and antibodies raised harvested from host fluids. The whole antibodies so induced can be used directly as combining sites, or they may be cleaved with pepsin or papain as is well known to provide F(ab')2 or Fab portions that are used as combining sites. The antibody combining sites produced can be used in diagnostic assays to detect the presence of the protein antibody or as therapeutic agents for passive immunoprophylaxis.

An animal infected by a leukemia-associated virus can be treated with antibody combining sites preferably as whole antibodies raised to the synthetic polypeptides of the present invention. The antibody combining sites are administered in a unit dose having an effective amount of sites dispersed in a physiologically tolerable diluent such as saline.

An effective amount of such antibodies varies depending on the reactivity and type of the antibodies, but generally about 1 milligram to about 50 milligrams of antibody per kilogram animal weight is considered effective. In the case of mice and murine leukemia virus, 1.5 milligrams of IgG antibody in ascites fluid has been found to be effective in prolonging survival. Se "Monoclonal Antibodies" ed. Kennett et al., Plenum Press (1980). The antibodies can be given intravenously or intraperitoneally, with eeveral administrations given at three to seven day intervals. The antibodies can also can be given in conjunction with surgical treatment.

The antibodies can be obtained from sera of a second animal, different from the first animal to be treated, by raising antibodies to the polypeptides of this invention. The antibodies can also be obtained from monoclonal sources such as ascites fluid by preparing a hybridoma cell line using known techniques. Whole antibodies are preferred as the combining sites since they are capable of activating the complement system when an immune complex is formed.

The term "unit dose" refers to physically discrete units suitable as unitary dosages for animals, each unit containing a predetermined quantity of active material calculated to produce the desired therapeutic effect in association with the required diluent; i.e., carrier, or vehicle. The specifications for the novel unit dose of this invention are dictated by and are directly dependent on (a) the unique characteristics of the active material and the particular therapeutic effect to be achieved, and (b) the limitations inherent in the art of compounding such active material for therapeutic use in animals, as disclosed in detail in the specification, these being features of the present invention.

Poly-specificity and cross-reactivity among the various types or serotypes of leukemia-associated viruses are improved by use of an antigenic polypeptide of this invention whose peptide sequence corresponds to a peptide sequence of at least more than one type or serotype. The sequence of such a polypeptide may not correspond substantially to a portion of the sequence of any one viral protein, but the polypeptide may nevertheless, when inoculated as part of a vaccine into an animal host, induce production of antibodies that immunoreact with a plurality of viruses.

III. IN VITRO ASSAYS

To examine the ability of various peptide sequences to induce the production of in vitro neutralizing antibodies, synthetic polypeptides corresponding to the sequences labeled in FIGS. 1, 2, and 3 were made and injected into rabbits and/or cats to produce desired antibodies. The harvested antibodies were then assayed for their ability to neutralize active FeLV-B viruses in vitro.

The peptide sequences identified in FIGS. 1-3 by "I" and "C" prefix designations were made according to the FeLV-B peptide sequence listed immediately below each designation, with the exception of where a "C" appears at the terminus in which case the peptide sequence is the FeLV sequence plus a terminal cysteine residue. For example, sequence 18B, corresponds substantially to the amino acid residue sequence of positions 17 through 24 of the gp70 protein of FeLV-B, but has a cysteine residue at its carboxy-terminus (position 25 of gp70) as opposed to an asparagine residue (N) listed direttly below for FeLV-B. All of the polypeptides synthesized had a cysteine residue of at least one terminus. One special case is the sequence designated C16B that extends from the carboxy-terminus of the gp70 to the amino-terminus of the p15E protein.

Immunizations

The polypeptides discussed below were synthesized chemically as discussed before. The polypeptides were then coupled to the protein carrier keyhole limpet hemocyanin (KLH) previously reacted with MBS through a cysteine residue usually at the carboxy-terminus of the polypeptide to form conjugates. The polypeptide was linked to the protein carrier by addition of the cysteine sulfur atom to the double bond of the reaction product between the carrier and MBS, following the general procedure described by Lieu et al., supra. Each of the above polypeptide-carrier conjugates was used without further purification.

Control sera were obtained from both rabbits and cats by bleeding just prior to initial immunization. The rabbits were then immunieed with 300-400 micrograms of conjugate in complete Freund's adjuvant (CFA), in incomplete Freund's adjuvant (IFA) and in alum (5 milligrams/milliliter) on days 0, 14 or 21 respectively.

In addition to the adjuvants, the vaccine also contained a physiologically tolerable diluent such as water, or phosphate-buffered saline (pH 7.4). Vaccine stock solutions were prepared with CFA or IFA as follows: An amount of conjugate sufficient to provide the desired amount of polypeptide per inoculation was dissolved in phosphate-buffered saline (PBS). Equal volumes of CFA or IFA were then mixed with the conjugate solution to provide an inoculum containing conjugate, water and adjuvant solution in which the water to oil ratio was 1:1. The mixture was thereafter homogenized to provide the vaccine stock solution.

Two groups of cats were immunized using either a high unit dose or a low unit dose protocol. Cats in the high unit dose protocol were immunized with 4 milligrams of conjugate in 1.4 milliliters of Montanide/Draekeol (M/D) (S.E.P.P.I. Co, Paris, France) adjuvant on days 0, 21, 42 and 280. Cats in the low unit dose protocol were immunized with 0.4 milligrams of conjugate in 1.4 milliliters of M/D adjuvant on days 0, 21, 42 and 280.

Cat immunizations consisted of one intramuscular injection. Cats were bled 2, 4, 8, 10, 12, 18, 40, 42 weeks after the last immunization and in some cases were further boosted w/ FeLVB in M/D.

Rabbit immunization consisted of 4 subcutaneous injections, one on each shoulder and hip. Rabbits were bled 7 days after the last immunization and in some cases were further boosted with conjugate in alum and bled as necessary. The collected blood was allowed to clot overnight and then centrifuged to obtain the sera used in the assays discussed below.

Neutralization Assays

In order to test large numbers of anti-polypeptide antisera two in vitro assays were used for FeLV-B virus that measure viral inactivation (neutralization) by immunoreactions between the harvested antibodies and live virus particles. The assays are reproducible and yield a percent reduction in virus producing foci between control sera and anti-polypeptide antibody.

The dog thymus cell line Cf2th that is available from the American Tissue Type Culture Collection under designation ATCC CRL 1430 is susceptible to FeLV infection and was used as viral host in this assay. Cf2th cells were grown in Minimum Eagels Medium (MEM) supplemented with 10 percent fetal calf serum, penicillin (100 units/milliliter), streptomycin (100 grams/milliliter), 4 millimolar (mM) L-glutamine, 1 mM Na-pyruvate. Following trypsinization with 0.025 percent trypsin in phosphate-buffered saline (PBS) and washing in MEM, $3 \times 10^5$ cells were added to tissue culture petri dishes (Falcon #3003) and were incubated overnight at 37 degrees C. in an atmosphere of 5 percent $CO_2$.

FeLV-B virus was immunoreacted with control sera and anti-peptide antisera in separate containers by admixing 5 microliters of either anti-polypeptide antisera or control sera with 100 microliters of MEM containing 400 focus-forming units of FeLV-B. The mixture is incubated at 37 degrees C. in a 5 percent $CO_2$ atmosphere for 40 minutes. The reaction was terminated by adding a solution of 5 milliliters of MEM containing 10 micrograms per milliliter hexadimethrine bromide available under the designation Polybrene P4515 from Sigma Chemical Co. of St. Louis, Missouri. The resulting mixturewwas then used to inoculate the Cf2th cultures.

The Cf2th cultures were inoculated by replacing the overnight growth MEM with 5 milliliters of the mixture. This mixture was replaced after 24 hours and the cultures incubated in MEM an additional 4 days at 37 degrees C. in a 5 percent $CO_2$ atmosphere. The cultures were then terminated by aspirating off the MEM, washing 3 times with 10 milliliters of PBS and allowing the monolayer to dry.

Virus-producing cell foci in the monolayer were detected using either a radioimmune assay (RIA) or an enzyme linked immunosorbent assay (ELISA). In both procedures, the infected cell monolayers were transferred and fixed onto a nitrocellulose solid matrix to form a solid support. This assay was performed by pre-wetting a nitrocellulose disc designated BA85 from Schleicher & Schuel of Ohio in PBS, placing the wetted disc over the monolayer and pressing firmly so as to transfer the cells from the petri dish onto the disc. The cells were fixed on the disc by placing the disc in Amido Black Dye [0.045 percent Naphthol Blue Black (Sigma N3005), 4 percent methanol, 10 percent acetic acid] for 1 minute and then destained (45 percent methanol, 10 percent acetic acid) for 5 minutes. Non-specific binding sites were then blocked by incubating the discs in BLOTTO [Bovine Lacto Transfer Technique Optimizer, 5 percent weight per volume non-fat dry milk, 0.01 percent Antifoam A Emulsion (a 30 percent aqueous emulsion of a silicone polymer containing anionic emulsifiers, Sigma A5758), 0.0001 percent merthiolate (Sigma T5125) in PBS] overnight at 4 degrees C. See Johnson and Elder J. Exp. Med., 159:1751–56 (1983).

In both the RIA and ELISA procedures, the blocked discs (solid supports) were then admixed with a first amplifying antibody; i.e., goat-anti-FeLV whole virus antibodies, so as to form a solid/liquid phase immunoreaction admixture. Each disc was placed in 5 milliliters of fresh BLOTTO with 50 microliters of goat-anti-FeLV whole virus antiserum and incubated for a time sufficient for the goat-anti-FeLV antibodies to immunoreact with any FeLV present on the discs (3 hours at 20 degrees C. while shaking). The solid and liquid phases were separated, and the solid phase discs were washed with 5 milliliters of BLOTTO 3 times for 15 minutes each, thereby separating unimmunoreacted antibodies from goat-anti-FeLV/FeLV immunoreaction products (primary immunoreactants) bound to the discs.

In the RIA procedure, each primary immunoreactant containing disc was placed in 5 milliliters of BLOTTO containing 5 microliters of rabbit-anti-goat antisera as a second amplifying antibody to form a solid/liquid phase admixture. That admixture was maintained for a time period sufficient fof an immunoreactant to form between (incubated at 20 degrees C. for 1 hour with shaking) rabbit-anti-goat antibodies and any goat anti-FeLV antibodies present on the discs as primary immunoreactants, thereby forming secondary immunoreactants. After incubation, the discs were again washed 3 times with BLOTTO for 15 minutes each.

Goat-anti-FeLV whole virus antiserum may be prepared by injecting FeLV virus particles into goats and recovering the sera.

The rabbit-anti-goat antisera was prepared by injecting rabbits as described above using purified goat gamma globulin as antigen.

To detect virus producing cell foci using the RIA procedure, *Staphylococcus aureus* Protein A was labeled with $^{125}I$, and 5 milliliters of BLOTTO containing 2.5 microliters of the $^{125}I$-labeled Protein A was admixed with the discs, with the admixtures being maintained for a time period of 1 hour at 20 degrees C. with shaking. This allowed the labeled Protein A to bind with the bound rabbit-anti-goat antibodies. The discs were again washed in BLOTTO as above and additionally washed with lithium chloride buffer [0.5M LiCl (L-121, Fisher Scientic, Pittsburgh, Pennsylvania), 0.1M Tris Base (Sigma T1503)] for 30 minutes and finally water for 30 minutes. The discs were dried and exposed to Kodak XRP-1 x-ray film available from Eastman Kodak Company of Rochester, New York.

To detect virus producing cell foci using the ELISA procedure, the above described discs containing primary immunoreactants were first immunoreacted with a second amplifying antibody. This was done by admixing 5 milliliters of BLOTTO containing 5 microliters of rabbit anti-goat IgG antibodies (Cappel Laboratories, Malvern, PA), so as to form a solid/liquid immunoreaction admixture. The solid/liquid admixtures so prepared were maintained for a time period of 3 hours at 20 degrees C. sufficient for the liquid phase second antibodies (rabbit anti-goat IgG) to immunoreact with the solid phase bound goat-anti-FeLV antibodies to form secondary immunoreactants. After immunoreaction, the solid and liquid phases were separated and the discs were washed 3 times as previously described.

An indicating means-containing reagent in the form of peroxidase labeled goat anti-rabbit IgG antibodies was used to detect the presence of secondary immunoreactants. Five milliliters of BLOTTO containing 10 microliters of peroxidase labeled goat anti-rabbit IgG (Cappel Laboratories) were admixed with the above described secondary immunoreactant containing discs. The solid/liquid admixtures so formed were maintained for a time period of 3 hours at 20 degrees C. sufficient for the peroxidase labeled indicating antibodies to immunoreact with any second amplifying antibodies present. The solid and liquid phase were then separated and the discs were washed 3 times as previously described.

Subsequently, the discs were admixed with 5 milliliters of freshly prepared developing solution. The developing solution was prepared by admixing 4 milliliters of 1M sodium acetate, pH 5.9, 37 milliliters $H_2O$, 8 milliliters of 4-chloro-2-naphthol (3 milligrams/milliliter in ethanol) and 30 microliters of 30% hydrogen peroxide. The disc/developing solution admixture was maintained at 20 degrees C. for a period sufficient to visualize the presence of indicating means-containing reagent immunologically bound to the discs, e.g., for about 30–45 minutes.

The RIA and ELISA were used as initial screening assays and were performed using a single control serum and anti-polypeptide antibodies at either a 1:20 or 1:10 dilution. Results of screening rabbit anti-polypeptide antisera by RIA are listed in Table 1 with antiserum designation corresponding to the polypeptides identified in FIGS. 1-3. The percent neutralization is calculated from the number of foci on any given disc treated with an antiserum compared to the number of foci on a control disc treated with control serum. Table I lists percent neutralization or neutralizing index of each antiserum made to (induced by) the polypeptides identified in FIGS. 1-3.

TABLE I

PERCENT NEUTRALIZATION OF FeLV-B VIRUS BY RABBIT ANTI-PEPTIDE ANTISERA RAISED TO POLYPEPTIDES SHOWN ON FIGS. 1-3

| Antiserum | Percent Neutralization |
|---|---|
| I3B | 0 |
| I4B | 17 |
| I5B | 4 |
| I6B | 56 |
| I7B | 83 |
| I8B | 0 |
| I10B | 73 |
| I21B | 5 |
| I26B | 45 |
| I27B | 43 |
| I28B | — |
| C1B | 0 |
| C2B | 0 |
| C4B | 23 |
| C5B | 17 |
| C6B | 23 |
| C7B | 0 |
| C8B | 32 |
| C9B | 4 |
| C10B | 26 |
| C11B | 31 |
| C12B | 0 |
| C13B | 7 |
| C14B | 68 |
| C15C | 40 |
| C15D | 32 |
| C16B | 20 |
| C18B | 64 |
| FeLV-1 | 0 |

From the above data, I6B, I7B, I10B, C14B, and C18B were selected for further study because they showed neutralization in excess of 50 percent at the 1:20 dilution. Other polypeptides studied having neutralization indices of less than 50 percent but nevertheless showing neutralization such as I4B, I28B, I26B, C8B, C6B, and C16B are also part of the present invention. As discussed above, C12B even though it does not show any in vitro neutralization of the virus, does produce antibodies having a high avidity against FeLV-B.

Titrations

Rabbit anti-peptide antibodies that demonstrated a greater than 50 percent neutralization at a 1:20 dilution in the RIA screening procedure were studied further using serial dilutions in that RIA. The results of this assay are shown in Table II.

TABLE II

PERCENT NEUTRALIZATION OF FeLV-B VIRUS BY DILUTIONS OF RABBIT ANTI-POLYPEPTIDE ANTISERA

| Antiserum | Dilution | | | | |
|---|---|---|---|---|---|
| | 1:5 | 1:10 | 1:15 | 1:20 | 1:40 |
| I10 | 93 | 91 | 89 | 73 | — |
| C14 | 86 | 79 | 76 | 68 | — |
| C18 | 92 | 75 | 67 | 64 | 53 |
| I6 | 83 | 76 | 62 | 56 | 17 |
| I7 | 90 | 93 | 86 | 83 | — |

In addition to the RIA neutraliaation assays of FeLV-B, similar neutralization assays were also done with FeLV-B2 and FeLV-C. C18B rabbit anti-polypeptide sera at a 1:5 dilution exhibited a 73 percent neutralization of FeLV-B2 and a 97 percent neutralization of FeLV-C virus. Ascan be seen from FIG. 3, the portion of the FeLV-B2 small envelope protein homologous to the FeLV-B over this region has one conservative substitution, an aspartic residue for the glutamic residue of FeLV-B. Even with this substitution, cross-reactivity between the different strains and serotypes of FeLV has been demonstrated.

Anti-polypeptide antibodies induced by immunizing cats as described hereinabove were screened using the ELISA virus neutralizing assay procedure. The results of the screening are listed in Table III below, with the antiserum designation again corresponding to the polypeptides identified in FIGS. 1-4. The percent neutralization was calculated by the same procedure used in Table 1.

TABLE III

PERCENT NEUTRALIZATION OF FELV-B VIRUS BY CAT ANTI-PEPTIDE ANTISERA RAISED TO POLYPEPTIDES SHOWN ON FIGS. 1-4

| Antiserum | | Cat Code | Percent Neutralization (Weeks after Third Boost) | | |
|---|---|---|---|---|---|
| | | | 2 | 4 | 12 |
| I6B | 0.4[1] | A | 12 | (0)[2] 38 | (0) 41 (0) |
| | 0.4 | B | 2 | (0) 32 | (0) 38 (0) |
| | 4.0 | U | 9 | (0) 11 | (0) 23 (10) |
| | 4.0 | V | 58 | (56) 46 | (32) 62 (26) |
| I7B | 0.4 | C | 9 | 53 | |
| | 0.4 | D | 0 | 10 | |
| | 4.0 | S | 10 | 0 | |
| | 4.0 | T | 33 | 0 | |
| C18B | 0.4 | G | 0 | 44 | |
| | 0.4 | H | 0 | 0 | |
| | 4.0 | P | 0 | 8 | |
| C14B | 0.4 | I | 0 | 35 | |
| | 0.4 | J | 15 | 21 | |
| | 4.0 | M | 0 | 0 | |
| | 4.0 | N | 0 | 0 | |
| I10B | 0.4 | K | 71 | 7 | |
| | 0.4 | L | 26 | 39 | |
| | 4.0 | Q | 13 | 0 | |
| | 4.0 | R | — | 0 | |
| 1024-3B | 0.4 | LLE1 | 7 | — | |
| | 0.4 | LLE2 | 52 | 24[3] | (0) |
| | 0.4 | LLE3 | 25 | 12[3] | (1) |
| I26B | 0.4 | LLE4 | 41 | 33[3] | (26) |
| | 0.4 | MQ1 | 36 | 26[3] | (0) |
| | 0.4 | MQ2 | 4 | — | |

[1]Number of milligrams of conjugate used per immunization, 0.4 milligrams being the low unit dose protocol and 4.0 milligrams being the high unit dose protocol as described herein.
[2]The numbers in parenthesis indicate percent neutralization after blocking of antibody with homologous polypeptide.
[3]These antisera were harvested three weeks after the second immunizing injection.

Western Blotting

The rabbit anti-peptide antibodies were examined using the Western Blot technique to confirm their predicted specificity for either the gp70 or p15E envelope proteins. The viral proteins were separated by gradient (5-17.5 percent) SDS-polyacrylamide gel electrophoresis. See Laemmli, *Nature*, 227:680-685 (1980) and Towbin, et al., *Proc. Natl. Acad. Sci. USA*, 76:4350-4354 (1979).

Proteins were electrophoretically transferred to nitrocellulose (Schleicher & Schuel, BA85) as described by Towbin et al., *Proc. Nat'l. Academy of Science*, 76:4350-4354 (1976), using an electroblot apparatus (E. C. Apparatus Corp. of Jacksonville, Florida) with buffer consisting of 25 millimolar Tris Base, 192 millimolar glycine, 20 percent methanol and 0.1 percent sodium dodecyl sulfate (pH 8.3). Following the transfer, the nitrocellulose was blocked in BLOTTO to reduce non-specific binding. The blots were reacted with 100 microliters of anti-peptide antibody in 10 milliliters of BLOTTO for 3 hours and then washed 3 times for 1 hour with 50 milliliters of fresh BLOTTO.

Anti-peptide antibodies bound to specific viral proteins were detected by reacting the blots with 20 microliters of $^{125}$I labeled Protein A in 10 milliliters of BLOTTO for 1 hour. The blots were then washed in 50 milliliters of fresh BLOTTO for 15 minutes 4 times and then under a continuous flow of water for 20 minutes.

TABLE IV
SPECIFICITY OF ANTI-PEPTIDE ANTISERA TO THE PROTEINS OF THE ENVELOPE GENE OF FeLV-B

| Peptide | Peptide Sequence[1] | Viral Protein Bound |
|---|---|---|
| I10B | CDIIGNTWNPSDQEPFPGYG | gp70 |
| C14B | CIGTVPKTHQALCNETQQGHT | gp70 |
| C18B | TDIQALEESISALEKSLTSLSE | p15E |
| I6B | AKLRERLKQRQQLF | p15E |
| I7B | DSQQGWFEGWFNKSPWFTTLISS | p15E |

[1]Sequences are shown from left to right and in the direction of amino-terminus to carboxy-terminus. Cysteine residues utilized for coupling to a carrier are not shown.

As can be seen from Table IV, above, the various anti-polypeptide sera reacted with and bound specifically to the envelope protein gp70 or p15E from which their respective polypeptide sequences were taken. Thus, the produced antibodies not only are properly specific to FeLV, but also are properly specific to their respective envelope proteins.

The data presented hereinabove indicate that there is at least one region within gp70 where antisera against two polypeptides adjacently located in the native molecule (i.e., I26B and C8B) display some virus neutralizing activity. Those data suggest the possibility that a single antigenic determinant domain may have been split into two regions during peptide design. To examine whether or not this may have occurred, a series of peptides whose amino acid residue sequences overlap portions of both the I26B and C8B peptides were synthesized (FIG. 4), and used in antisera crossreactivity studies.

An antiserum to peptide 1024-3B was raised in a rabbit by immunization as previously described. Using the ELISA virus neutralization procedure described hereinbefore, the rabbit anti-1024-3B so produced demonstrated a greater than 90 percent reduction in the number of virus-producing cell foci.

Polypeptide ELISA

Rabbit anti-polypeptide antisera to peptides 1024-3B, I26B, I26B and C8B were then examined for their ability to immunoreact with each of the overlap peptides shown in FIG. 4 using a solid phase-bound (affixed) polypeptide ELISA. In the polypeptide ELISA, peptides of the present invention were adsorbed (affixed) onto a solid matrix of a polyvinyl chloride microtiter plate to form a solid support. Adsorption was accomplished by admixing 50 microliters of peptide at 0.02 milligrams/milliliter in carbonate buffer (0.1M NaHCO$_3$, pH 9.0) in each well, and maintaining the wells at 37 degrees C. for a time period sufficient for the buffer to evaporate and deposit the peptide onto the well walls; i.e., about 16 hours.

After adsorption, non-specific binding sites were blocked by admixture of 50 microliters of PBS containing 5 percent (v/v) heat inactivated newborn calf serum in each well, and maintaining those admixtures for a time period of 2 hours at 37 degrees C. The wells were then washed 6 times with PBS.

To each well were admixed 100 microliters of heat inactivated study or control serum to form a solid/liquid phase immunoreaction admixture and contact anti-polypeptide antibodies present in the sera with the solid phase-affixed polypeptides. The solid/liquid immunoreaction admixtures were maintained for a time period sufficient for the liquid phase receptor molecules to immunoreact with the solid phase-affixed polypeptides (2 hours at 37 degrees C.). The maintained solid/liquid phase admixtures were separated. The solid phase wells were then washed 6 times with PBS containing 0.05 percent Tween 20 to separate the unbound portion of the study sample from any solid phase bound immunoreaction products.

An indicating means-containing reagent, in the form of peroxidase labeled goat-anti-rabbit IgG (Cappel Laboratories) diluted 1:4000 in T Wash [2.5% (v/v) newborn calf serum, 0.2% BSA, 0.05% Tween 20, 150 mM NaCl, 0.50 mM Tris-HCl (pH 7.6) was admixed in the wells to detect the presence of immuoreaction products and form a still further solid/liquid phase admixture. After maintaining the admixture for a time period of 2 hours at 37 degrees C. for immunoreaction and binding of the indicating means-containing reagent with solid phase-bound rabbit anti-polypeptide IgG present, the wells were washed 6 times with PBS containing 0.05 percent (v/v) Tween 20.

The presence of goat anti-rabbit IgG antibodies bound to rabbit anti-polypeptide/polypeptide immunoreaction products was detected by providing o-phenylenediamine (OPD) developing solution (Abbott Laboratories) as peroxidase substrate. One hundred microliters of OPD developing solution containing 0.01 percent H$_2$O$_2$ were admixed in each well and incubated for a time period of 30 minutes at room temperature. The color developing reaction was stopped by admixing 50 microliters of 4N H$_2$SO$_4$ in each well. The amount of indicating means-containing immunoreaction product present was immediately quantitated by measuring the absorbance of each well at 490 nanometers using a Dynatech ELISA plate reader.

The results of examining the ability of rabbit anti-polypeptide antisera to peptides for their ability to immunoreact with the overlap peptides shown in FIG. 4 are presented in Table V below.

TABLE V

ABILITY OF RABBIT ANTIPOLYPEPTIDE ANTISERA TO IMMUNOREACT WITH I26B-C8B OVERLAP PEPTIDES IN THE POLYPEPTIDE ELISA

| Overlap Polypeptide[1] | Rabbit Antiserum to: | | |
|---|---|---|---|
| | I26B | 1024-3B | C8B |
| 1052-15B | + | + | + |
| 1052-14B | + | + | − |
| 1052-13B | + | + | + |
| 1024-3B | + | + | ± |
| I26B | + | + | − |
| C8B | − | + | + |

[1] The position of each overlapping peptide used as target antigen is shown in FIG. 4.

The above antisera were considered to have positively immunoreacted (+) with a target peptide if they displayed a four fold higher titer than the normal (unimmunized) control antiserum. Antisera were considered to have weakly immunoreacted (±) with a target peptide if they displayed only a two fold higher titer than the normal control.

To further characterize the neutralizing antigenic determinant domains contained in peptides I26B and C8B, peptide blocking (inhibition) studies were performed using the ELISA virus neutralizing assay described hereinbefore. In these studies, heat inactivated rabbit antisera to polypeptides I26B and C8B were first immunoreacted with either their inducing, peptide immunogen (I26B or C8B respectively) or with peptide 1024-3B before the antisera were immunoreacted with FeLV-B virus as previously described.

The blocking immunoreaction was performed by initially admixing 10 microliters of antiserum and either 10 microliters of peptide solution at 1 milligram per milliliter $H_2O$, or 100 microliters of peptide solution at 0.1 milligrams per milliliter $H_2O$. The admixtures were then maintained for a time period sufficient to permit anti-polypeptide receptor molecules to immunoreact with antigenic determinant domains located on the peptides (30 minutes at 37 degrees C.). The admixtures were then examined for virus neutralizing activity as previously described. Successful immunoreaction between anti-polypeptide antibodies and polypeptide blocked or inhibited further immunoreaction between the antibody and FeLV-B virus during the virus neutralization assay, thereby decreasing the antiserum's total neutralizing activity. The results of this peptide inhibition study are presented in Table VI below.

TABLE VI

PERCENT NEUTRALIZATION OF FELV-B VIRUS BY RABBIT ANTI-PEPTIDE ANTISERA WHEN BLOCKED WITH HOMOLOGOUS OR OVERLAP POLYPEPTIDES

| Peptide Antiserum | Blocking Polypeptide | Percent Neutralization |
|---|---|---|
| none | none | 0 |
| I26B | none | 95 |
| I26B | I26B | 15 |
| I26B | 1024-3B | 25 |
| C8B | none | 52 |
| C8B | C8B | 0 |
| C8B | 1024-3B | 40 |

It is believed that in vitro virus neutralization by antibodies may occur as a result of two different mechanisms. In the first, neutralizing antibodies immunologically bind to the surface of the virus in a manner that sterically hinders any subsequent attachment by the virus to its cellular host, thereby preventing infection. In the second, neutralizing antibodies immunoreact with the virus to form an immune complex that activates the immune serums's complement components. The activated complement components subsequently lyse and destroy the virus thereby preventing infection.

The role of complement in virus neutralization by rabbit anti-polypeptide antisera to peptides I7B and I26B was examined. This was accomplished by running parallel virus neutralization assays in which complement levels in the rabbit antisera were controlled by first heat inactivating native complement present in the sera and then admixing known amounts of exogenously supplied rabbit complement to the virus neutralizing immunoreaction admixture.

Aliquots of rabbit anti-I7B and rabbit anti-I26B were heat inactivated by incubation at 56 degrees C. for 30 minutes. The heat inactivated antisera were then diluted 1:5 and 1:100 in MEM, respectively. Five microliters of antiserum and 0, 5, 10 or 20 microliters of rabbit complement (Cappel Laboratories) were then admixed with FeLV-B virus, immunoreacted and used to infect CF2th cells as previously described except that complement-containing inoculates were removed from the cell cultures after two hours so as to prevent complement-mediated lysis of the cells.

The results of this study, are presented in Table VII below.

TABLE VII

PERCENT NEUTRALIZATION OF FELV-B VIRUS BY HEAT INACTIVATED RABBIT ANTI-PEPTIDE ANTISERA IN THE PRESENCE OR ABSENCE OF EXOGENOUS RABBIT COMPLEMENT

| Peptide Antiserum | Microliters of Added Complement | Percent Neutralization |
|---|---|---|
| I7B | 0 | 64 |
| I7B | 0 | 54 |
| I7B | 5 | 41 |
| I7B | 20 | 44 |
| I26B | 0 | 14 |
| I26B | 0 | 6 |
| I26B | 10 | 53 |
| I26B | 10 | 76 |
| I26B* | 10 | 15 |
| I26B* | 10 | 18 |

*Antiserum was blocked with its homologous peptide (I26B), as previously described, before immunoreaction with virus and complement.

As can be seen from Table VII, in vitro virus neutralization by rabbit anit-I26B was increased from an average of 10 percent to an average of 64.5 percent with the addition of 10 microliters of complement to the assay, whereas the addition of complement to the rabbit anti-I7B assays lowered the percent neutralization.

Virus ELISA

An ELISA using whole FeLV as solid phase target antigen was developed to screen antipeptide antisera for the ability to recognize the native glycosylated gp70's of different FeLV isolates. Both the FeLV-B strain previously described and a FeLV field strain obtained from Dr. E. Hoover at Colorado State University were used in the virus ELISA.

FeLV-B and FeLV field strain virus stocks were prepared by harvesting 24 hour tissue culture supernatants from virus infected CF2th cell cultures. The supernatants were first centrifuged for 10 minutes at 8000 rpm in a Sorval GSA rotor (Sorvall Instruments, Claremont, CA) to pellet large cellular debris. The resulting virus-containing supernatant was then pelleted through a 29 percent sucrose cushion (w/v in TNE; 0.50 mM Tris HCl 150 MaCl 1.0 mM EDTA) by centrifugation for 2 hours at 40,000 rpm in a Ti45 rotor (Beckman Instruments, Palo Alto, CA). The virus pellets were resuspended in TNE and their protein concentration determined using a Bio-Rad Protein Assay kit according to the manufacturer's instructions (Bio-Rad, Richmond, CA).

The virus antigen was then adsorbed (affixed) onto a solid matrix in the form of a polyvinylchloride microtiter plate to form a solid support. Adsorption was accomplished by admixing about 0.1 to about 1.0 micrograms of viral protein in 0.1M NaHCO$_3$, pH 9.0, in each well, and incubating the wells at 37 degrees C. for a time period sufficient for the buffer to evaporate and deposit the virus onto the well walls; i.e, about 16 hours. The wells were further processed, immunoreacted and quantititated as previously desribed in the polypeptide ELISA procedure. The rabbit anti-polypeptide antisera used in these studies were heat inactivated and used in both blocked and unblocked condition as previously described.

The results of examining the rabbit anti-polypeptide antisera to peptides I26B, C8B, I6B and I7B in the virus ELISA using FeLVB as target antigen are graphically illustrated in FIG. 5. All five of the anti-polypeptide antisera examined immunoreacted with the FeLV-B derived native glycosylated gp70 envelope protein when compared to the negative control normal rabbit serum.

In FIG. 6, the results obtained in the FeLV-B ELISA are graphically compared with the results obtained for the same anti-polypeptide antisera in the previously described polypeptide ELISA. FIG. 6 indicates that the rabbit antiserum to C18B has a particularly high affinity for the FeLV-B strain of virus as compared to its inducing polypeptide (C18B).

The results of screening rabbit anti-polypeptide antisera to I26B, 1024-3B, C8B, C18B and I6B against the FeLV field strain in the virus ELISA are graphically illustrated in FIG. 7. FIG. 7 demonstrates the anti-polypeptide antisera to I26B, 1024-3B, C18B and I6B strongly recognized the native gp70 envelope protein of the field strain but that rabbit anti-C8B only weakly immunoreacts with this virus. These results are graphically compared in FIG. 8 with the results obtained for the same anti-polypeptide antisera in the previously described polypeptide ELISA.

IV. DIAGNOSTICS

The polypeptides, antibody combining sites and methods of the present invention may be used in the preparation of diagnostic tests, such as immunoassays. Such diagnostic techniques include, for example, enzyme immune assay, enzyme multiplied immunoassay technique (EMIT), enzyme-linked immunosorbent assay (ELISA), radioimmune assay (RIA), fluorescence immune assay, either single or double antibody techniques, and other techniques in which either the antibody combining site or the antigen is labeled with some detectable tag. See generally *Enzyme Immunoassay*, by Maggio, CRC Press (1981).

A diagnostic system of the present invention to detect a leukemia-associated virus antigen contains the biologically active antibody combining sites raised to a polypeptide of this invention. The system also includes an indicating means for signalling the presence of an immunoreaction between the combining sites and the antigen. The indicating means allows the immunoreaction to be detected and preferably measurement of the amount of that immunoreaction detected. When admixed with a body component such as serum, urine or a tissue extract, the combining sites immunoreact with the antigen to form an immunoreactant, and the indicating means signals that immunoreaction.

For ease of description, whole antibodies will be described for use as combining sites. In some cases where rheumatiod factors may be a problem, Fab or F(ab')$_2$ portions may be used.

On exemplary embodiment is an ELISA in which a predetermined amount of body component such as serum is coated on a test well to form a solid phase-affixed antigen. Non-specific binding sites on the wells are blocked with a protein such as BSA. Antibodies of this invention, generally at about 0.5 picograms to about 1.2 micrograms such as those raised in rabbits are utilized in an aqueous liquid composition. The composition and its antibodies are admixed with the wells to form a solid/liquid phase admixture. That admixture is incubated in the wells using well-known techniques for a time period sufficient for the antibodies to immunoreact with antigen. After separating the solid and liquid phases as by rinsing away any un-immunoreacted antibodies, second antibodies raised to the antibodies such as goat anti-rabbit antibodies is then similarly admixed and incubated in a solution in the test well. The second antibodies are labeled by being linked to an enzyme such as alkaline phosphatase. Generally about 50 nanograms to about 120 nanograms of second labeled antibodies are used.

After this second incubation, any excess of the second antibodies is rinsed out leaving any phosphatase-linked goat-antirabbit antibodies that bound to the first antibodies within the test well. Subsequent admixture of an enzyme substrate such as p-nitrophenyl phosphate provides a yellow-colored signal that a leukemia-associated virus antigen was present in the body component. Measurement of the optical density of the resulting colored solution after a predetermined period of time has elapsed provides a quantitative measurement of the amount of enzyme-linked antibodies that were bound, and thereby a measurement of the amount of leukemia-associated viral antigen that was present in the body component.

In place of an enzyme and substrate, a radioactive element such as $^{125}$I may be bonded to an antibody of this invention using well known techniques to provide the indicating means. See generally, *Methods in Immunology and Immunochemistry* Academic Press (1967). Here, for example, the body component may be precoated in a sample tube followed by incubation with the radioactive combining sites and rinsing of excess combining sites from the tube. Radioactivity remaining in the tube after rinsing provides the signal that an immunoreactant was formed. Where it is desirable to eliminate the wash step, an EMIT system can be used where the immunoreaction alters the activity of the antigen-linked enzyme.

Another embodiment of the invention are competition assays which include a first reagent and a second reagent in separate containers. The first reagent contains synthetic antigenic polypeptide of this invention. The second reagent contains antibody combining sites in biologically active form that immunoreact with that polypeptide. The combining sites can be made from antibodies raised to the polypeptide in the first reagent. A means for indicating the presence of an immunoreaction between the polypeptide and antibodies as discussed above is also included either in a separate container or with a reagent. Where the labeling means is an enzyme and its substrate, a separate container for the substrate is preferred, while separate containers need not be used for radiolabeled combining sites.

In usual practice, the body component is admixed and pre-incubated with the antibody combining sites to form a liquid admixture, with the period of pre-incubation being a sufficient time for an immunoreactant to form. That liquid admixture is then admixed and incubated, as described before, with a polypeptide that is immobilized as a solid phase as by being bound to the walls of a well, thus forming a solid/liquid phase admixture. Non-specific binding sites on the well walls are typically blocked with a protein such as BSA after polypeptide immobilization and prior to formation of the solid/liquid phase admixture. Separating the phases as by rinsing of the well to remove any combining site-leukemia-associated virus antigen complex leaves an immunoreactant of the polypeptide and combining sites whose presence and amount may be signalled and measured by the indicating means.

Alternatively, the antibody combining sites can be immobilized and labeled polypeptides used in a competitive assay. Still another method is the Western Blot Assay described in detail above.

The use of whole, intact, biologically active antibodies for the combining sites is not necessary in many diagnostic systems such as the competition assay discussed immediately above. Rather, only the biologically active idotype-containing, antigen binding and recognition combining site of the antibody molecule may be needed. Illustrative of such combining sites are those known as Fab and F(ab')$_2$ antibody portions that are prepared by well-known enzymatic reactions on typically whole antibodies.

The present invention has been described with respect to preferred embodiments. It will be clear to those skilled in the art that modifications and/or variations of the disclosed subject matter can be made without departing from the scope of the invention set forth herein.

What is claimed is:

1. A synthetic polypeptide containing about 8 to about 40 amino acid residues in a sequence corresponding to a peptide sequence of an antigenic determinant domain of an envelope protein that is homologous to the small envelope protein p15E of FeLV-B from about position 70 to about position 95 taken from the amino-terminus of p15E.

2. The synthetic polypeptide of claim 1 whose sequence corresponds substantially to said peptide sequence of an antigenic determinant domain of said envelope protein that is homologous to the small envelope protein 15E of FeLV-B from about position 70 to about position 95 taken from the amino-terminus of p15E.

3. The synthetic polypeptide of claim 1 wherein the induced antibodies in sera neutralize live leukemia-associated virus particles in vitro testing using live animal cells, the neutralization being at least 25 percent as compared with control sera.

4. The synthetic polypeptide of claim 1 wherein the virus is a feline leukemia-associated virus.

5. The synthetic polypeptide of claim 1 wherein the virus is a human leukemia-associated virus.

6. The synthetic polypeptide of claim 1 including a peptide sequence corresponding to a formula selected from the group consisting of:

RRGLDILFL(W)Q(K or E)E(Q) GGL; and

Q(K or E)E(Q)GGLCA(K)AL K(Q)E(I)E(Q)C wherein the amino acid residues in parentheses are each an alternative to the immediately preceding amino acid residue in the sequence, and wherein each sequence is taken from left to right in the direction from amino-terminus to carboxy-terminus.

7. The synthetic polypeptide of claim 1 containing about 12 to about 20 amino acid residues.

8. A polypeptide comprising about 8 to about 40 amino acid residues corresponding to an antigenic domain of an envelope protein of a leukemia-associated virus;

said envelope protein being characterized as the smaller of two proteins encoded by the env gene of said virus and having the following structural features:

(a) three Cys residues;

(i) the first of said Cys residues being spaced about 80 to 90 residues away from the amino-terminus of said small envelope protein;

(ii) the second of said Cys residues being spaced about seven residues toward the carboxy-terminus of said small envelope protein from said first Cys residue, and (iii) the third of said Cys residues being spaced still further toward the carboxy-terminus of said small envelope protein than said second Cys residue;

(b) a leucine-rich polypeptide segment that contains about 10 amino acid residues of which the majority are Leu or Ile residues and is located toward the carboxy-terminus of said small envelope protein from said second Cys residue; and (c) a polypeptide segment containing a sequence of about 15 amino acid residues that is substantially identical in the viruses denominated FeLV-B, M-MuLV, AKV, and ATLV, and is located adjacent to and on the amino-terminal side of said first Cys residue;

said polypeptide including a sequence of at least 8 amino acid residues that corresponds to the amino acid residue sequence located in said smaller envelope protein between a position about 15 amino acid residues toward the amino-terminus from said first Cys residue of said protein and said leucine-rich segment located toward the carboxy-terminus from said second cysteine residue of said smaller envelope protein, said polypeptide being free from immunosuppressive peptide sequences, and having the capacity when injected into an animal host as a conjugate bound to an antigenic carrier of inducing antibodies that immunoreact with a leukemia-associated virus.

9. The polypeptide of claim 8 having a peptide sequence corresponding to at least a portion of the peptide sequence of said small envelope protein between a segment about 10 amino acid residues toward the carboxy-terminus from two cysteine residues spaced about seven residues apart, and said leucine-residue-rich segment toward the carboxy-terminus from said two cysteine residues.

10. The polypeptide of claim 8 having a peptide sequence that corresponds to at least a portion of the fifty amino acid residue sequence on the amino-terminus side of said leucine-residue-rich segment of said virus small envelope protein.

11. A polypeptide having a peptide sequence containing about 8 to about 40 amino acid residues and corresponding substantially to a peptide sequence of an antigenic determinant domain of an envelope protein homologous to a portion of a FeLV-B protein from about position 70 to about position 95 from the amino-terminus of said small envelope protein, and whose sequence corresponds to a FeLV-B polypeptide which as a conjugate of the FeLV-B polypeptide bound to a carrier induces the production of antibodies which in sera neutralize live FeLV-B virus particles in vitro from infecting live dog thymus cells from cell line Cf2th when compared to control sera.

12. The polypeptide of claim 11 including a peptide sequence corresponding substantially to a formula selected from the group consisting of:
   (1) RRGLDILFLQEGGLCAALKEEC;
   (2) RRGLDELFLQIGGLC; and
   (3) QEGGLCAALKEEC;
wherein each sequence is taken from left to right in the direction from amino-terminus to carboxy-terminus.

13. An antigenic polymer having repeating units comprising a plurality of antigenic polypeptides in accordance with claim 1 linked together.

14. A synthetic polypeptide containing about 8 to about 40 amino acid residues, said polypeptide including an amino acid residue sequence of at least 8 residues that corresponds to a sequence of the formula
   QNRRGLDILFL(W)Q(K or E)E(Q)GGLC A(K-)ALK(Q)E(I)E(Q)CF
wherein the amino acid residues in parentheses are each an alternative to the immediately preceding amino acid residue in the sequence, and wherein said sequence is taken from left to right and in the direction from amino-terminus to crrboxy-terminus, said polypeptide being free from immunosuppressive peptide sequences, and having the capacity when injected into an animal host as a conjugate bound to an antigenic carrier of inducing antibodies that immunoreact with a leukemia-associated virus.

15. The synthetic polypeptide of claim 14 whose at least 8 residues correspond to a sequence of the formula
   QNRRGLDILFLQEGGLCAALKEECF.

16. The synthetic polypeptide of claim 14 that contains about 12 to about 20 amino acid residues.

17. A synthetic polypeptide containing about 8 to about 40 amino acid residues, said polypeptide including an amino acid residue sequence of at least 8 residues that corresponds to a sequence of the formula (1) Q(K)V(Y or I or R)M(Q or T or L)T(N or D)I (L or S)T(G)PP(R)Q(V)A(P or S) M(I)GPNL(P)V-L(I)P(A or S or T)D; and
   (2) DQ(R)K(L or R)P(S or Q)P(F)S(P or L) R(L or S)Q(P or K)S(N or R or V)Q (P or K)I(L or T)E(P or R or V or M) S(K or L)R(P or S)V(A or R) T(K or S or P)V(A or R)T(K or S or P) P(S or V)H(P or T or Q)

wherein the amino acid residues in parentheses are each an alternative to the immediately preceding amino acid residue in the sequence, and wherein said sequence is taken from left to right and in the direction from amino-terminus to carboxy-terminus, said polypeptide being free from immunosuppressive peptide sequences, and having the capacity when injected into an animal host as a conjugate bound to an antigenic carrier of inducing antibodies that immunoreact with a leukemia-associated virus.

18. The synthetic polypeptide of claim 17 whose at least 8 residues correspond to a sequence of the formula
   QVMTITPPQAMGPNLVLPDQKPPSRQSQ IESRVTPH.

19. The synthetic polypeptide of claim 17 that contains about 12 to about 20 amino acid residues.

20. An antigenic polypeptide having a peptide sequence, taken from left to right in the direction from amino-terminus to carboxy-terminus, represented by the formula:
   QVMTITPPQAMGPNLVLP.

21. An antigenic polypeptide having a peptide sequence, taken from left to right in the direction from amino-terminus to carboxy-terminus, represented by the formula:
   DQKPPSRQSQIESRVTP.

22. An antigenic polypeptide having a peptide sequence, taken from left to right in the direction from amino-terminus to carboxy-terminus, represented by the formula:
   RRGLDILFLQIGGLC.

23. An antigenic polypeptide having a peptide sequence, taken from left to right in the direction from amino-terminus to carboxy-terminus, represented by the formula:
   QIGGLCAALKEEC.

24. A synthetic polypeptide containing about 8 to about 40 amino acid residues that correspond to the sequence of the small envelope protein p15E of FeLV-B from about position 70 to position 95 taken from the amino-terminus of p15E.

* * * * *